(12) United States Patent
Dodd et al.

(10) Patent No.: US 9,320,748 B2
(45) Date of Patent: Apr. 26, 2016

(54) IMMUNOLOGICALLY USEFUL ARGININE SALTS

(71) Applicant: Novartis AG, Basel (CH)

(72) Inventors: Stephanie Kay Dodd, Ayer, MA (US); Siddhartha Jain, Troy, NY (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/381,513

(22) PCT Filed: Mar. 7, 2013

(86) PCT No.: PCT/EP2013/054548
§ 371 (c)(1),
(2) Date: Aug. 27, 2014

(87) PCT Pub. No.: WO2013/131985
PCT Pub. Date: Sep. 12, 2013

(65) Prior Publication Data
US 2015/0125475 A1    May 7, 2015

Related U.S. Application Data

(60) Provisional application No. 61/608,011, filed on Mar. 7, 2012.

(51) Int. Cl.
| | | |
|---|---|---|
| *C07F 9/6561* | (2006.01) | |
| *A61K 39/39* | (2006.01) | |
| *A61K 31/675* | (2006.01) | |
| *A61K 39/00* | (2006.01) | |

(52) U.S. Cl.
CPC ............... *A61K 31/675* (2013.01); *A61K 39/39* (2013.01); *C07F 9/6561* (2013.01); *A61K 2039/55511* (2013.01)

(58) Field of Classification Search
CPC ......................... C07D 471/04; A61K 31/4375
USPC ...................................... 546/10, 23
See application file for complete search history.

(56) References Cited

U.S. PATENT DOCUMENTS

| | | | |
|---|---|---|---|
| 6,113,911 | A | 9/2000 | Binz et al. |
| 6,699,474 | B1 | 3/2004 | Cerny |
| 7,309,494 | B2 | 12/2007 | Corvaia et al. |
| 2012/0177681 | A1 * | 7/2012 | Singh et al. ................. 424/193.1 |

FOREIGN PATENT DOCUMENTS

| | | |
|---|---|---|
| WO | WO-9318150 A1 | 9/1993 |
| WO | WO-9527787 A1 | 10/1995 |
| WO | WO-9601272 A1 | 1/1996 |
| WO | WO-9601273 A1 | 1/1996 |
| WO | WO-9725429 A1 | 7/1997 |
| WO | WO-0037494 A2 | 6/2000 |
| WO | WO-0202606 A2 | 1/2002 |
| WO | WO-03010317 A1 | 2/2003 |
| WO | WO-03049762 A2 | 6/2003 |
| WO | WO-03097091 A2 | 11/2003 |
| WO | WO-2004032958 A1 | 4/2004 |
| WO | WO-2005002619 A2 | 1/2005 |
| WO | WO-2005084306 A2 | 9/2005 |
| WO | WO-2006089264 A2 | 8/2006 |
| WO | WO-2006091517 A2 | 8/2006 |
| WO | WO-2006138004 A2 | 12/2006 |
| WO | WO-2007060548 A2 | 5/2007 |
| WO | WO-2007110700 A2 | 10/2007 |
| WO | WO-2008020330 A2 | 2/2008 |
| WO | WO-2009050586 A1 | 4/2009 |
| WO | WO-2010119343 A2 | 10/2010 |
| WO | WO-2010140119 A1 | 12/2010 |
| WO | WO2010144734 | * 12/2010 |
| WO | WO-2011024072 A2 | 3/2011 |
| WO | WO-2011027222 A2 | 3/2011 |
| WO | WO-2011049677 A1 | 4/2011 |
| WO | WO-2012031140 A1 | 3/2012 |
| WO | WO-2012103421 A1 | 8/2012 |
| WO | WO2013030378 | * 3/2013 |

OTHER PUBLICATIONS

Arginine-Rich Molecular Transporters for Drug Delivery: Role of Backbone Spacing in Cellular Uptake Jonathan B. Rothbard et al 2002.*
I-Arginine stimulates immune response in chickens immunized with intermediate plus strain of infectious bursal disease vaccine Chandrakant Tayade et al , 2006.*

* cited by examiner

*Primary Examiner* — Rita Desai
(74) *Attorney, Agent, or Firm* — Helen Lee; Virginia Campen

(57) ABSTRACT

The invention is in the field of salt forms of an immunopotentiator compound and their formulation for in vivo use. In particular the invention relates to arginine salts.

17 Claims, 8 Drawing Sheets

SEQUENCE LISTING

<160> NUMBER OF SEQ ID NOS: 5

<210> SEQ ID NO 1
<211> LENGTH: 327
<212> TYPE: PRT
<213> ORGANISM: Artificial Sequence
<220> FEATURE:
<223> OTHER INFORMATION: Antigen derived from Neisseria meningitidis

<400> SEQUENCE: 1

```
Ala Thr Asn Asp Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
        35                  40                  45

Thr Ala Ala Asp Val Glu Ala Asp Asp Phe Lys Gly Leu Gly Leu Lys
    50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
    130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
    210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
        275                 280                 285

His Asp Thr Arg Leu Asn Gly Leu Asp Lys Thr Val Ser Asp Leu Arg
    290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325
```

<210> SEQ ID NO 2
<211> LENGTH: 644
<212> TYPE: PRT
<213> ORGANISM: Artificial Sequence
<220> FEATURE:
<223> OTHER INFORMATION: Antigen derived from Neisseria meningitidis

<400> SEQUENCE: 2

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Pro Ser Ala Gly Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335
```

```
Leu Pro Gly Gly Ser Tyr Ala Leu Arg Val Gln Gly Glu Pro Ser Lys
                340                 345                 350

Gly Glu Met Leu Ala Gly Thr Ala Val Tyr Asn Gly Glu Val Leu His
            355                 360                 365

Phe His Thr Glu Asn Gly Arg Pro Ser Pro Ser Arg Gly Arg Phe Ala
        370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
    450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
        515                 520                 525

Ala Asn Leu Gln Ser Gly Ser Gln His Phe Thr Asp His Leu Lys Ser
530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
        595                 600                 605

Asp Phe Ser Thr Thr Ile Asp Arg Thr Lys Trp Gly Val Asp Tyr Leu
610                 615                 620

Val Asn Val Gly Met Thr Lys Ser Val Arg Ile Asp Ile Gln Ile Glu
                625                 630                 635                 640

Ala Ala Lys Gln

<210> SEQ ID NO 3
<211> LENGTH: 434
<212> TYPE: PRT
<213> ORGANISM: Artificial Sequence
<220> FEATURE:
<223> OTHER INFORMATION: Antigen derived from Neisseria meningitidis

<400> SEQUENCE: 3

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
            20                  25                  30
```

```
Leu Arg Ile Glu Thr Thr Ala Arg Ser Tyr Leu Arg Gln Asn Asn Gln
         35                  40                  45

Thr Lys Gly Tyr Thr Pro Gln Ile Ser Val Val Gly Tyr Asp Arg His
 50                  55                  60

Leu Leu Leu Leu Gly Gln Val Ala Thr Glu Gly Glu Lys Gln Phe Val
 65                  70                  75                  80

Gly Gln Ile Ala Arg Ser Glu Gln Ala Glu Gly Val Tyr Asn Tyr
                 85                  90                  95

Ile Thr Val Ala Ser Leu Pro Arg Thr Ala Gly Asp Ile Ala Gly Asp
                100                 105                 110

Thr Trp Asn Thr Ser Lys Val Arg Ala Thr Leu Leu Gly Ile Ser Pro
                115                 120                 125

Ala Thr Arg Ala Arg Val Lys Ile Val Thr Tyr Gly Asn Val Thr Tyr
        130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
        195                 200                 205

Gly Leu Gln Ser Leu Thr Leu Asp Gln Ser Val Arg Lys Asn Glu Lys
        210                 215                 220

Leu Lys Leu Ala Ala Gln Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
        275                 280                 285

Gln Thr Glu Gln Ile Gln Asp Ser Glu His Ser Gly Lys Met Val Ala
        290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
                340                 345                 350

Ala Lys Gln Gly Asn Gly Lys Ile Glu His Leu Lys Ser Pro Glu Leu
        355                 360                 365

Asn Val Asp Leu Ala Ala Ala Asp Ile Lys Pro Asp Gly Lys Arg His
        370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
            420                 425                 430

Lys Gln
```

<210> SEQ ID NO 4
<211> LENGTH: 686
<212> TYPE: PRT
<213> ORGANISM: Artificial Sequence
<220> FEATURE:
<223> OTHER INFORMATION: Antigen derived from Neisseria meningitidis

<400> SEQUENCE: 4

```
Met Val Ser Ala Val Ile Gly Ser Ala Ala Val Gly Ala Lys Ser Ala
1               5                   10                  15

Val Asp Arg Arg Thr Thr Gly Ala Gln Thr Asp Asn Val Met Ala
            20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asp Arg His
        50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Arg Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
        195                 200                 205

Gly Leu Gln Ser Leu Thr Leu Asp Gln Ser Val Arg Lys Asn Glu Lys
    210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
        275                 280                 285

Gln Thr Glu Gln Ile Gln Asp Ser Glu His Ser Gly Lys Met Val Ala
    290                 295                 300

Lys Arg Gln Phe Arg Ile Gly Asp Leu Gly Gly Glu His Thr Ala Phe
305                 310                 315                 320

Asn Gln Leu Pro Asp Gly Lys Ala Glu Tyr Arg Gly Thr Ala Phe Gly
                325                 330                 335

Ser Asp Asp Ala Gly Gly Lys Leu Thr Tyr Thr Ile Asp Phe Thr Lys
            340                 345                 350

Lys Gln Gly Asn Gly Lys Ile Glu His Leu Lys Ser Pro Glu Leu Asn
        355                 360                 365

Val Glu Leu Ala Ser Ala Glu Ile Lys Ala Asp Gly Lys Ser His Ala
```

```
                370             375             380
Val Ile Leu Gly Asp Val Arg Tyr Gly Ser Glu Glu Lys Gly Ser Tyr
385                 390                 395                 400

Ser Leu Gly Ile Phe Gly Gly Arg Ala Gln Glu Val Ala Gly Ser Ala
                405                 410                 415

Glu Val Lys Thr Val Asn Gly Ile Arg His Ile Gly Leu Ala Ala Lys
            420                 425                 430

Gln Gly Ser Gly Gly Gly Val Ala Ala Asp Ile Gly Ala Gly Leu
        435                 440                 445

Ala Asp Ala Leu Thr Ala Pro Leu Asp His Lys Asp Lys Gly Leu Gln
450                 455                 460

Ser Leu Thr Leu Asp Gln Ser Val Arg Lys Asn Glu Lys Leu Lys Leu
465                 470                 475                 480

Ala Ala Gln Gly Ala Glu Lys Thr Tyr Gly Asn Gly Asp Ser Leu Asn
                485                 490                 495

Thr Gly Lys Leu Lys Asn Asp Lys Val Ser Arg Phe Asp Phe Ile Arg
                500                 505                 510

Gln Ile Glu Val Asp Gly Gln Leu Ile Thr Leu Glu Ser Gly Glu Phe
            515                 520                 525

Gln Val Tyr Lys Gln Ser His Ser Ala Leu Thr Ala Phe Gln Thr Glu
530                 535                 540

Gln Ile Gln Asp Ser Glu His Ser Gly Lys Met Val Ala Lys Arg Gln
545                 550                 555                 560

Phe Arg Ile Gly Asp Leu Gly Gly Glu His Thr Ala Phe Asn Gln Leu
                565                 570                 575

Pro Asp Gly Lys Ala Glu Tyr Arg Gly Thr Ala Phe Gly Ser Asp Asp
                580                 585                 590

Ala Gly Gly Lys Leu Thr Tyr Thr Ile Asp Phe Thr Lys Lys Gln Gly
            595                 600                 605

Asn Gly Lys Ile Glu His Leu Lys Ser Pro Glu Leu Asn Val Glu Leu
        610                 615                 620

Ala Ser Ala Glu Ile Lys Ala Asp Gly Lys Ser His Ala Val Ile Leu
625                 630                 635                 640

Gly Asp Val Arg Tyr Gly Ser Glu Glu Lys Gly Ser Tyr Ser Leu Gly
                645                 650                 655

Ile Phe Gly Gly Arg Ala Gln Glu Val Ala Gly Ser Ala Glu Val Lys
                660                 665                 670

Thr Val Asn Gly Ile Arg His Ile Gly Leu Ala Ala Lys Gln
            675                 680                 685

<210> SEQ ID NO 5
<211> LENGTH: 776
<212> TYPE: PRT
<213> ORGANISM: Artificial Sequence
<220> FEATURE:
<223> OTHER INFORMATION: Antigen derived from Neisseria meningitidis

<400> SEQUENCE: 5

Met Gly Pro Asp Ser Asp Arg Leu Gln Gln Arg Arg Val Ala Ala Asp
1               5                   10                  15

Ile Gly Ala Gly Leu Ala Asp Ala Leu Thr Ala Pro Leu Asp His Lys
                20                  25                  30

Asp Lys Ser Leu Gln Ser Leu Thr Leu Asp Gln Ser Val Arg Lys Asn
            35                  40                  45

Glu Lys Leu Lys Leu Ala Ala Gln Gly Ala Glu Lys Thr Tyr Gly Asn
```

```
                50                  55                  60
Gly Asp Ser Leu Asn Thr Gly Lys Leu Lys Asn Asp Lys Val Ser Arg
 65                  70                  75                  80

Phe Asp Phe Ile Arg Gln Ile Glu Val Asp Gly Gln Leu Ile Thr Leu
                 85                  90                  95

Glu Ser Gly Glu Phe Gln Ile Tyr Lys Gln Asp His Ser Ala Val Val
                100                 105                 110

Ala Leu Gln Ile Glu Lys Ile Asn Asn Pro Asp Lys Ile Asp Ser Leu
                115                 120                 125

Ile Asn Gln Arg Ser Phe Leu Val Ser Gly Leu Gly Gly Glu His Thr
130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
                180                 185                 190

Gln Asn Val Glu Leu Ala Ala Ala Glu Leu Lys Ala Asp Glu Lys Ser
                195                 200                 205

His Ala Val Ile Leu Gly Asp Thr Arg Tyr Gly Ser Glu Glu Lys Gly
210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Gly Gly Val Ala Ala Asp Ile Gly Ala
                260                 265                 270

Gly Leu Ala Asp Ala Leu Thr Ala Pro Leu Asp His Lys Asp Lys Gly
                275                 280                 285

Leu Gln Ser Leu Thr Leu Asp Gln Ser Val Arg Lys Asn Glu Lys Leu
                290                 295                 300

Lys Leu Ala Ala Gln Gly Ala Glu Lys Thr Tyr Gly Asn Gly Asp Ser
305                 310                 315                 320

Leu Asn Thr Gly Lys Leu Lys Asn Asp Lys Val Ser Arg Phe Asp Phe
                325                 330                 335

Ile Arg Gln Ile Glu Val Asp Gly Gln Leu Ile Thr Leu Glu Ser Gly
                340                 345                 350

Glu Phe Gln Val Tyr Lys Gln Ser His Ser Ala Leu Thr Ala Phe Gln
                355                 360                 365

Thr Glu Gln Ile Gln Asp Ser Glu His Ser Gly Lys Met Val Ala Lys
                370                 375                 380

Arg Gln Phe Arg Ile Gly Asp Ile Ala Gly Glu His Thr Ser Phe Asp
385                 390                 395                 400

Lys Leu Pro Glu Gly Gly Arg Ala Thr Tyr Arg Gly Thr Ala Phe Gly
                405                 410                 415

Ser Asp Asp Ala Gly Gly Lys Leu Thr Tyr Thr Ile Asp Phe Ala Ala
                420                 425                 430

Lys Gln Gly Asn Gly Lys Ile Glu His Leu Lys Ser Pro Glu Leu Asn
                435                 440                 445

Val Asp Leu Ala Ala Ala Asp Ile Lys Pro Asp Gly Lys Arg His Ala
450                 455                 460

Val Ile Ser Gly Ser Val Leu Tyr Asn Gln Ala Glu Lys Gly Ser Tyr
465                 470                 475                 480
```

-continued

```
Ser Leu Gly Ile Phe Gly Gly Lys Ala Gln Glu Val Ala Gly Ser Ala
            485                 490                 495
Glu Val Lys Thr Val Asn Gly Ile Arg His Ile Gly Leu Ala Ala Lys
            500                 505                 510
Gln Gly Ser Gly Pro Asp Ser Asp Arg Leu Gln Arg Arg Val Ala
            515                 520                 525
Ala Asp Ile Gly Thr Gly Leu Ala Asp Ala Leu Thr Ala Pro Leu Asp
    530                 535                 540
His Lys Asp Lys Gly Leu Lys Ser Leu Thr Leu Glu Asp Ser Ile Pro
545                 550                 555                 560
Gln Asn Gly Thr Leu Thr Leu Ser Ala Gln Gly Ala Glu Lys Thr Phe
                565                 570                 575
Lys Ala Gly Asp Lys Asp Asn Ser Leu Asn Thr Gly Lys Leu Lys Asn
            580                 585                 590
Asp Lys Ile Ser Arg Phe Asp Phe Val Gln Lys Ile Glu Val Asp Gly
            595                 600                 605
Gln Thr Ile Thr Leu Ala Ser Gly Glu Phe Gln Ile Tyr Lys Gln Asn
        610                 615                 620
His Ser Ala Val Val Ala Leu Gln Ile Glu Lys Ile Asn Asn Pro Asp
625                 630                 635                 640
Lys Thr Asp Ser Leu Ile Asn Gln Arg Ser Phe Leu Val Ser Gly Leu
                645                 650                 655
Gly Gly Glu His Thr Ala Phe Asn Gln Leu Pro Gly Gly Lys Ala Glu
                660                 665                 670
Tyr His Gly Lys Ala Phe Ser Ser Asp Asp Pro Asn Gly Arg Leu His
            675                 680                 685
Tyr Ser Ile Asp Phe Thr Lys Lys Gln Gly Tyr Gly Arg Ile Glu His
            690                 695                 700
Leu Lys Thr Leu Glu Gln Asn Val Glu Leu Ala Ala Ala Glu Leu Lys
705                 710                 715                 720
Ala Asp Glu Lys Ser His Ala Val Ile Leu Gly Asp Thr Arg Tyr Gly
                725                 730                 735
Ser Glu Glu Lys Gly Thr Tyr His Leu Ala Leu Phe Gly Asp Arg Ala
            740                 745                 750
Gln Glu Ile Ala Gly Ser Ala Thr Val Lys Ile Gly Glu Lys Val His
            755                 760                 765
Glu Ile Gly Ile Ala Gly Lys Gln
770                 775
```

IMMUNOLOGICALLY USEFUL ARGININE SALTS

RELATED APPLICATIONS

This application is the U.S. National Phase of International Application No. PCT/EP2013/054548, filed Mar. 7, 2013 and published in English, which claims the benefit of U.S. Provisional Application No. 61/608,011, which was filed Mar. 7, 2012. The complete contents of each of the foregoing applications are hereby incorporated herein by reference for all purposes.

SEQUENCE LISTING

The instant application contains a Sequence Listing and is hereby incorporated by reference in its entirety. Said ASCII copy, created on Dec. 15, 2014, is named PAT054848-US-PCT_SEQListing and is 25,037 bytes in size.

TECHNICAL FIELD

The invention is in the field of salt forms of an immunopotentiator compound and their formulation for in vivo use. In particular the invention relates to arginine salts.

SEQUENCE LISTING

This application contains a Sequence Listing which has been submitted via EFS-Web and is hereby incorporated by reference in its entirety. The ASCII copy, created on Mar. 4, 2013, is named 54848_SeqListing.TXT, and is 24,989 bytes in size.

BACKGROUND ART

Early detection of specific classes of pathogens is accomplished by the innate immune system with the help of pattern recognition receptors (PRRs). The detected pathogens include viruses, bacteria, protozoa and fungi, and each constitutively expresses a set of class-specific, mutation-resistant molecules called pathogen-associated molecular patterns (PAMPs).

Toll-like receptors (TLRs) are an important family of PRRs and are widely expressed on innate immune cells, including dendritic cells (DCs), macrophages, mast cells, neutrophils, endothelial cells and fibroblasts. TLRs have broad specificity for conserved molecular patterns shared by bacteria, viruses and parasites.

A number of different TLRs have been characterized. These TLRs bind and become activated by different ligands, which in turn are located on different organisms or structures. The development of immunopotentiator compounds that are capable of eliciting responses in specific TLRs is of interest in the art.

For example, reference 1 discloses a broad class of small molecule immunopotentiators (SMIPs) that are TLR7 agonist compounds. Immunogenic compositions and pharmaceutical compositions comprising these compounds are also disclosed in the reference.

It is an object of the invention to provide salt forms of a specific TLR7 compound having formula (I) shown below which have improved properties, such as improved solubility and photo-stability and reducing the gelling nature of the salt when compared to the free base.

DISCLOSURE OF THE INVENTION

The invention relates to salts of an immunopotentiator compound of formula (I) shown below, said compound being an agonist of human TLR7, 3-(5-amino-2-(2-methyl-4-(2-(2-(2-phosphonoethoxy)ethoxy)ethoxy)phenethyl)benzo[f][1,7]naphthyridin-8-yl)propanoic acid.

Formula (I)

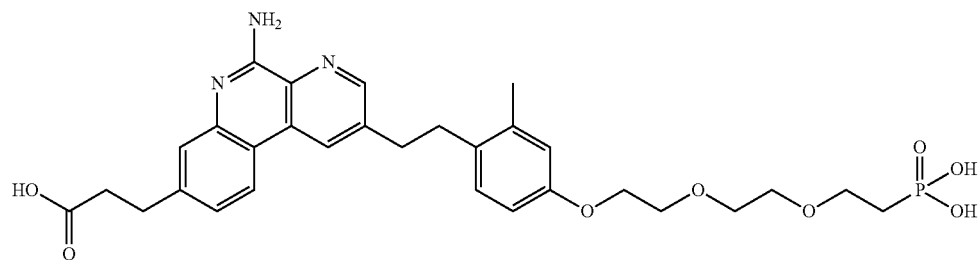

In particular, the invention relates to arginine salts of the compound of formula (I). In studies on different salt forms of the above compound the arginine salt was surprisingly found to be the most favourable across a range of test criteria such as solubility, yield, photo-stability, stability of the counter ion and thermal-stability at physiological pH. In particular, the arginine salts of the present invention display improved photo-stability in solution when compared to the free base compound of formula (I).

Owing to the multi-basic nature of both the compound of formula (I) and arginine, the salts of the invention may exist at various stoichiometries with respect to the number of moles of the compound of formula (I) and the arginine counter ion. For example, the stoichiometry of the compound of formula (I):arginine can be 1:1, 1:2 or 1:3. Preferably, the stoichiometry is 1:1.

The salts of the invention may be solvated or unsolvated. For example, the salts may exist as hydrous or anhydrous forms. The salts may exist as mono or di-hydrates (i.e. containing 1 or 2 moles of water). Preferably, the salt is a monohydrate.

The arginine salts of the invention may exist as amorphous or crystalline solids. Alternatively, the salts exist as partially crystalline solids containing both amorphous and crystalline solids. In one aspect of the invention, the salts are substantially amorphous containing portions of short range order. In one embodiment, the crystalline form of the salt exhibits at least the following X-ray powder diffraction peaks, expressed in degrees 2Θ; 10, 14 and 18.5. The salt form may have an X-ray powder diffraction pattern substantially the same as that shown in FIG. 1. The $^{13}C$ and $^{15}N$ NMR spectra of the arginine salts of the present invention in the solid state are shown in FIGS. 1a and 1b respectively.

The invention also provides an arginine salt of the compound of formula (I) for use in therapy. The invention further provides the use of an arginine salt of the compound of formula (I) in the manufacture of a medicament for use in therapy. In each case, the therapy may be a method of raising an immune response in a subject.

A method of raising an immune response in a subject comprising the step of administering to the subject an arginine salt of the compound of formula (I) as described herein is also provided.

The PK/PD of immunopotentiators (and in particular TLR agonists) can be improved by adsorbing them to insoluble metal salts, such as aluminium salts (see reference 2). Stable adsorption of the compounds ideally takes place by ligand exchange via an adsorptive moiety, such as a phosphonate group, which can mediate adsorption. SMIPs having adsorptive moieties can retain their in vivo immunological activity when delivered in an adsorbed form, and so the improved PK/PD properties are not at the expense of activity. Adsorption of the compounds means that they have higher residence time at sites of intramuscular injection, thereby controlling the level of systemic exposure. High systemic exposure can elicit the production of high levels of proinflammatory cytokines in the blood, so higher residence time at an injection site can minimise the production of proinflammatory cytokines in the blood, thus improving safety and/or tolerability of the compounds.

This concept of improvement of PK/PD properties of immunopotentiators by adsorption to insoluble metal salts has applicability in the present invention. Thus, the invention provides a composition comprising an arginine salt of the compound of formula (I) as described herein and an insoluble metal salt. Preferably, the compound of formula (I) as described herein of the arginine salt is adsorbed on the insoluble metal salt. In one embodiment the composition includes a buffer.

The invention also provides a composition comprising an arginine salt of the compound of formula (I) as described herein, an insoluble metal salt and an immunogen. Preferably, the compound of formula (I) as described herein of the arginine salt of the composition is adsorbed on the insoluble metal salt.

In another aspect, the invention provides a process for preparing an arginine salt of the compound of formula (I) as described herein, wherein the process comprises the step of contacting the compound of formula (I) with arginine in a solvent, such a methanol. The process can further comprise crystallising the arginine salt, for instance via the addition of ethanol to the solvent (e.g. to methanol). In another aspect, the invention provides a process for preparing a crystalline form of an arginine salt of the compound of formula (I) as described herein, wherein the process comprises the step of contacting the arginine salt of a compound of formula (I) as described herein with a solvent, such as isopropanol or acetonitrile. The arginine may be L- or D-arginine or a racemic mixture. Preferably L-arginine is used.

In a further aspect, the invention provides a process for preparing an adjuvant complex, comprising a step of mixing an arginine salt of the compound of formula (I) with an insoluble metal salt such that the compound of formula (I) as described herein of the arginine salt adsorbs to the insoluble metal salt to form the complex. The invention also provides an adjuvant complex obtained or obtainable by this process. The complex can be mixed with an immunogen to provide an immunogenic composition.

In another aspect, the invention provides a process for preparing a sterile adjuvant complex, comprising the steps of: (i) mixing an arginine salt of the compound of formula (I) with an insoluble metal salt such that the compound of formula (I) as described herein of the arginine salt adsorbs to the insoluble metal salt to form the complex; and (ii) sterilising the complex. The invention also provides a sterile adjuvant complex obtained or obtainable by this process. The sterile complex can be mixed with an immunogen to provide an immunogenic composition. Sterilisation can be conveniently achieved by autoclaving (or similar procedures [3]).

The invention also provides a process for preparing a sterile adjuvant complex, comprising steps of: (i) sterilising a solution or suspension of an arginine salt of the compound of formula (I) as described herein; and (ii) combining the sterilised solution or suspension with a sterile insoluble metal salt. The invention also provides a process for preparing a sterile adjuvant complex, comprising steps of: (i) sterilising an insoluble metal salt; and (ii) combining the sterilised insoluble metal salt with a sterile solution or suspension of an arginine salt of the compound of formula (I) as described herein. The invention also provides a process for preparing a sterile adjuvant complex, comprising a step of combining a sterile solution or suspension of an arginine salt of the compound of formula (I) as described herein with a sterile insoluble metal salt. Sterilisation of the arginine salt solution/suspension can conveniently be achieved by sterile filtration, and this material can be prepared in concentrated form. Sterilisation of the insoluble metal salt can conveniently be achieved by autoclaving. The sterile insoluble metal salt will typically be an aqueous suspension. The invention also provides a sterile adjuvant complex obtained or obtainable by any one of the aforementioned processes.

According to another aspect, the invention provides a process for preparing an immunogenic composition, wherein the process comprises mixing an arginine salt of the compound of formula (I) as described herein, an insoluble metal salt, and an immunogen, thereby providing the immunogenic composition. The invention also provides an immunogenic composition obtained or obtainable by this process.

Arginine

Arginine is an α-amino acid having the formula shown below.

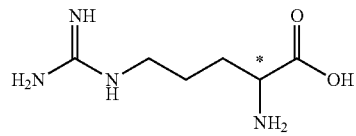

Arginine has a chiral centre (the carbon atom marked with an asterisk) and can exist in so called L or D forms. The L form of arginine has an absolute stereochemistry of S at its chiral centre whereas the D form has an absolute stereochemistry of R at its chiral centre.

Both L-arginine and D-arginine are capable of forming salts with acidic compounds owing to the basic properties of the guanidinium group. In some embodiments, the arginine salts of the invention are formed between the compound of formula (I) disclosed herein and L-arginine. In some embodiments the arginine salts of the invention are formed between the compound of formula (I) as described herein and D-arginine. Preferably, the arginine salt of the compound of formula (I) described herein is the L-arginine salt.

Insoluble Metal Salts

The immunopotentiator compound disclosed herein (i.e. the compounds of formula (I)) of the arginine salt forms can adsorb to insoluble metal salts, thereby forming an adsorbed complex. For instance, the immunopotentiator compound disclosed herein of the arginine salt forms can adsorb to insoluble calcium salts (e.g. calcium phosphate) or, preferably, to insoluble aluminium salts. Such aluminium salts have a long history of use in vaccines, as adjuvants for example. Aluminium salts which include hydroxide ions are the preferred insoluble metal salts for use with the present invention.

Thus the invention provides various embodiments in which the compound of formula (I) of the arginine salts disclosed herein is adsorbed to such insoluble metal salts.

Useful aluminium salts include, but are not limited to, aluminium hydroxide, aluminium oxyhydroxide, and aluminium hydroxyphosphates (including aluminium hydroxyphosphate sulfate). Such salts are described e.g. in chapters 8 and 9 of reference 4.

Preferred insoluble metal salts are aluminium oxyhydroxides and/or aluminium hydroxyphosphate. These have surface hydroxyl moieties which can readily undergo ligand exchange with the phosphonate group of the immunopotentiator compound to provide stable adsorption.

The adjuvants commonly known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at $1070\ cm^{-1}$ and a strong shoulder at $3090$-$3100\ cm^{-1}$ (chapter 9 of reference 4). The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{3+}$ at pH 7.4 have been reported for aluminium hydroxide adjuvants.

The adjuvants commonly known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a $PO_4^{3-}/Al^{3+}$ molar ratio between 0.3 and 1.2. Hydroxyphosphates can be distinguished from strict $AlPO_4$ by the presence of hydroxyl groups. For example, an IR spectrum band at $3164\ cm^{-1}$ (e.g. when heated to 200° C.) indicates the presence of structural hydroxyls (chapter 9 of reference 4).

The $PO_4^{3-}/Al^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4^{3-}/Al^{3+}$ molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{3+}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

In solution both aluminium phosphate and hydroxide adjuvants tend to form stable porous aggregates 1-10 μm in diameter [5].

A composition including the salt form of the invention adsorbed to an insoluble metal salt can also include a buffer (e.g. a phosphate or a histidine or a Tris buffer).

Because of the insolubility of adsorptive metal salts which are useful with the invention, compositions containing the adsorbed salt form of the invention will generally be suspensions having a cloudy appearance. This can mask contaminating bacterial growth and so a composition of the invention may include a preservative such as thiomersal or 2-phenoxyethanol. It is preferred that a composition should be substantially free from (e.g. <10 μg/ml) mercurial material e.g. thiomersal-free. Vaccines containing no mercury are more preferred.

A composition can include a mixture of both aluminium hydroxide and aluminium phosphate salts, and the arginine salt form of the compound of formula (I) disclosed herein may be adsorbed to one or both of these metal salts.

The concentration of $Al^{3+}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of <0.85 mg/dose is preferred. Because the inclusion of an arginine salt of the compound of formula (I) can improve the adjuvant effect of aluminium salts then the invention advantageously permits lower amounts of $Al^{3+}$ per dose, and so a composition of the invention can usefully include between 10 and 250 μg of $Al^{3+}$ per unit dose. Current pediatric vaccines typically include at least 300 μg $Al^{3\pm}$. In concentration terms, a composition of the invention may have an $Al^{3+}$ concentration between 10 and 500 μg/ml e.g. between 10-300 μg/ml, between 10-200 μg/ml, or between 10-100 μg/ml.

In general, when a composition includes both an arginine salt of the invention and an aluminium salt, the weight ratio of agonist to $Al^{3+}$ will be less than 5:1 e.g. less than 4:1, less than 3:1, less than 2:1, or less than 1:1. Thus, for example, with an $Al^{3+}$ concentration of 0.5 mg/ml the maximum concentration of an arginine salt of the invention would be 2.5 mg/ml. But higher or lower levels can be used; a lower mass of arginine salt than of $Al^{3+}$ is typical e.g. per dose, 100 μg of arginine salt with 0.2 mg $Al^{3+}$. A maximum of 2.5 mg of the compound of formula I per human unit dose (e.g. per 0.5 ml injection) is preferred.

Where a composition includes an arginine salt of the compound of formula (I) as described herein and an insoluble metal salt, it is preferred that at least 50% (by mass) of the immunopotentiator in the composition is adsorbed to the metal salt e.g. ≥60%, ≥70%, ≥80%, ≥85%, ≥90%, ≥92%, ≥94%, ≥95%, ≥96%, ≥97%, ≥98%, ≥99%, or even 100%. A minimum of 80% adsorption is typical, and at least 90% or 95% is preferred.

As discussed above, as a result of adsorption to an insoluble metal salt the in vivo behaviour of SMIPs can be modified. Thus an adsorbed SMIP can display a longer residence time (e.g. at least 2× longer) in muscle after intramuscular injection, relative to the same SMIP injected in non-adsorbed form. Some clearance can occur, but a detectable portion of the injected SMIP will still be present. Thus, for instance, an adsorbed SMIP can, when injected intramuscularly, still be present in the injected muscle at least 12 hours later e.g. 24 hours later.

In some embodiments, an adsorbed arginine salt can display a lower peak serum concentration, relative to the non-adsorbed form. This peak is usually expressed as a $C_{max}$ value. For instance, an adsorbed form can, when injected intramuscularly, have a lower serum $C_{max}$ value than when injected intramuscularly in non-adsorbed form (e.g. <95% of the non-adsorbed $C_{max}$, <80% of the non-adsorbed $C_{max}$, <50% of the non-adsorbed $C_{max}$, or even <30% of the non-adsorbed $C_{max}$).

In some embodiments, the adsorbed arginine salt can display a lower total systemic exposure after injection, relative to the same salt injected in non-adsorbed form. Levels of systemic exposure are usually expressed as AUC (area under the concentration-time curve) values (e.g. in nM·hr). Advantageously, for instance, an adsorbed SMIP can, when injected intramuscularly, have a lower serum AUC value in the 24 hours following injection than the same arginine salt when injected intramuscularly in non-adsorbed form (e.g. <90% of the non-adsorbed AUC, <80% of the non-adsorbed AUC, or even <50% of the non-adsorbed AUC, etc.).

Immunogens

Complexes of salt forms of the compound of formula (I) as described herein adsorbed to insoluble metals salts are useful during immunisation. An adsorbed complex of the invention can thus be used in conjunction with one or more immunogen(s). The complex and immunogen(s) can be provided as an admixture, or can be provided separately for use after mixing. In some embodiments, a salt form of the invention can be combined with an immunogen in the absence of an insoluble metal salt, and can thereafter either be administered to a mammal or can be combined with an insoluble metal salt for later administration to a mammal.

The invention can be used with a wide range of immunogens, for treating or protecting against a wide range of diseases. The immunogen may elicit an immune response that protects against a viral disease (e.g. due to an enveloped or non-enveloped virus), a bacterial disease (e.g. due to a Gram negative or a Gram positive bacterium), a fungal disease, a parasitic disease, an auto-immune disease, or any other disease. The immunogen may also be useful in immunotherapy e.g. for treating a tumour/cancer, Alzheimer's disease, or an addiction.

The immunogen may take various forms e.g. a whole organism, an outer-membrane vesicle, a polypeptide, a saccharide, a liposaccharide, a conjugate (e.g. of a carrier and a hapten, or of a carrier and saccharide or liposaccharide), etc. Where the immunogen is a polypeptide it will typically be a surface polypeptide e.g. an adhesin, hemagglutinin, envelope glycoprotein, spike glycoprotein, etc.

The immunogen may elicit an immune response against an influenza virus, including influenza A and B viruses. Various forms of influenza virus immunogen are currently available, typically based either on live virus or on inactivated virus. Inactivated vaccines may be based on whole virions, split virions, or on purified surface antigens. Influenza antigens can also be presented in the form of virosomes. Hemagglutinin is the main immunogen in current inactivated vaccines, and vaccine doses are standardised by reference to HA levels, typically measured by SRID. Existing vaccines typically contain about 15 µg of HA per strain, although lower doses can be used e.g. for children, or in pandemic situations, or when using an adjuvant. Fractional doses such as ½ (i.e. 7.5 µg HA per strain), ¼ and ⅛ have been used, as have higher doses (e.g. 3× or 9× doses [6,7]). Thus compositions may include between 0.1 and 150 µg of HA per influenza strain, preferably between 0.1 and 50 µg e.g. 0.1-20 µg, 0.1-15 µg, 0.1-10 µg, 0.5-5 µg, etc. Particular doses include e.g. about 45, about 30, about 15, about 10, about 7.5, about 5, about 3.8, about 3.75, about 1.9, about 1.5, etc. per strain. It is usual to include substantially the same mass of HA for each strain included in the vaccine e.g. such that the HA mass for each strain is within 10% of the mean HA mass per strain, and preferably within 5% of the mean. For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical. Rather than use SPF eggs as the substrate for viral growth, where virus is harvested from infected allantoic fluids of hens' eggs, cell lines that support influenza virus replication may be used. The cell line will typically be of mammalian origin e.g. MDCK. Influenza A virus immunogens may be from any suitable HA subtype strain e.g. H1, H3, H5, H7, H9 etc., such as a H1N1, H3N2 and/or H5N1 strain.

The immunogen may elicit an immune response against a *Candida* fungus such as *C. albicans*. For instance, the immunogen may be a β-glucan, which may be conjugated to a carrier protein. The glucan may include β-1,3 and/or β-1,6 linkages. Suitable immunogens include those disclosed in references 8 and 9.

The immunogen may elicit an immune response against a *Streptococcus* bacterium, including *S. agalactiae*, *S. pneumoniae* and *S. pyogenes*. For instance, the immunogen may be a capsular saccharide, which may be conjugated to a carrier protein. For *S. agalactiae* the saccharide may be from one or more of serotypes Ia, Ib, II, III, and/or V. For *S. pneumoniae* the saccharide may be from one or more of serotypes 1, 3, 4, 5, 6B, 7F, 9V, 14, 18C, 19F, and/or 23F. In addition to (or in place of) capsular saccharide immunogen(s), polypeptide immunogens may be used to elicit a protective anti-streptococcal immune response e.g. comprising RrgB, as disclosed in reference 10.

The immunogen may elicit an immune response against a *Staphylococcus* bacterium, including *S. aureus* or *S. epidermidis*. For instance, the immunogen may comprise an IsdA antigen, an IsdB antigen, a ClfA antigen, a ClfB antigen, a SdrD antigen, a Spa antigen, an EsxA antigen, an EsxB antigen, a Sta006 antigen, a hemolysin, and/or a Sta011 antigen. Suitable *S. aureus* immunogens and their combinations are disclosed in reference 11.

The immunogen may elicit an immune response against a meningococcal bacterium (*Neisseria meningitidis*). For instance, the immunogen may be a capsular saccharide, which may be conjugated to a carrier protein. Capsular saccharides are particularly useful for protecting against meningococcal serogroups A, C, W135 and/or Y. In addition to (or in place of) capsular saccharide immunogen(s), polypeptide immunogens and/or outer membrane vesicles may be used to elicit a protective anti-meningococcal immune response, particularly for use against serogroup B e.g. as disclosed in reference 12. A typical amount of capsular saccharide per unit dose of a vaccine is between 2.5-10 µg, although lower doses can be used with the invention due to the antigen-sparing nature of the adjuvants.

The immunogen may elicit an immune response against a hepatitis virus, such as a hepatitis A virus, a hepatitis B virus, a hepatitis C virus and/or a hepatitis E virus. For instance, the immunogen may be hepatitis B virus surface antigen (HBsAg). A typical amount of HBsAg per unit dose of a vaccine is between 5-20 μg, but lower doses can be used with the invention due to the antigen-sparing nature of the adjuvants.

The immunogen may elicit an immune response against a respiratory syncytial virus. Immunogens may be from a group A RSV and/or a group B RSV. Suitable immunogens may comprise the F and/or G glycoproteins or fragments thereof e.g. as disclosed in references 13 and 14.

The immunogen may elicit an immune response against a *Chlamydia* bacterium, including *C. trachomatis* and *C. pneumoniae*. Suitable immunogens include those disclosed in references 15-21.

The immunogen may elicit an immune response against an *Escherichia coli* bacterium, including extraintestinal pathogenic strains. Suitable immunogens include those disclosed in references 22-24.

The immunogen may elicit an immune response against a coronavirus, such as the human SARS coronavirus. Suitable immunogens may comprise the spike glycoprotein.

The immunogen may elicit an immune response against a *Helicobacter pylori* bacterium. Suitable immunogens include CagA [25-28], VacA [29,30], and/or NAP [31-33].

The immunogen may elicit an immune response against a *Corynebacterium diphtheriae* bacterium. Suitable immunogens include diphtheria toxoid ("DT"). A typical amount of DT per unit dose of a pediatric vaccine is between 15-30 Lf ("limes flocculating dose"), although lower doses can be used with the invention due to the antigen-sparing nature of the adjuvants. Lower amounts are also typical in adolescent or adult booster vaccines e.g. between 1-10 Lf/dose.

The immunogen may elicit an immune response against a *Clostridium tetani* bacterium. Suitable immunogens include tetanus toxoid ("TT"). A typical amount of TT per unit dose of a pediatric vaccine is between 5-15 Lf ("limes flocculating dose"), although lower doses can be used with the invention due to the antigen-sparing nature of the adjuvants. Lower amounts are also typical in adolescent or adult booster vaccines e.g. between 1-5 Lf/dose.

The immunogen may elicit an immune response against a *Bordetella pertussis* bacterium. Pertussis antigens are either cellular (whole cell, in the form of inactivated *B. pertussis* cells; 'wP') or acellular ('aP'). Where acellular antigens are used, one, two or (preferably) three of the following antigens are included: (1) detoxified pertussis toxin (pertussis toxoid, or 'PT'); (2) filamentous hemagglutinin ('FHA'); (3) pertactin (also known as the '69 kiloDalton outer membrane protein'). The PT may be chemically detoxified or may be a mutant PT in which enzymatic activity has been reduced by mutagenesis [34] e.g. the 9K/129G double mutant [35]. As well as PT, FHA and pertactin, it is also possible to include fimbriae (e.g. agglutinogens 2 and 3) in an acellular pertussis antigen component. A typical amount of PT in a pediatric vaccine is 10-30 μg/dose. A typical amount of FHA in a pediatric vaccine is 15-30 μg/dose. A typical amount of pertactin in a pediatric vaccine is 2-10 μg/dose. Lower doses can be used with the invention due to the antigen-sparing nature of the adjuvants. Lower amounts are also typical in booster vaccines e.g. ~3 times lower.

The immunogen may elicit an immune response against a *Haemophilus influenzae* type B bacterium ("Hib"). Suitable immunogens include conjugates of the Hib capsular saccharide ("PRP") e.g. conjugated to tetanus toxoid, diphtheria toxoid, the CRM197 derivative of diphtheria toxoid, *H. influenzae* protein D, and an outer membrane protein complex from serogroup B meningococcus. A typical amount of Hib conjugate (measured as saccharide) is between 2.5-15 μg per dose, although lower doses can be used with the invention due to the antigen-sparing nature of the adjuvants.

The immunogen may elicit an immune response against a poliovirus. Suitable immunogens include inactivated viruses. A typical composition will include three poliovirus antigens—poliovirus Type 1 (e.g. Mahoney strain), poliovirus Type 2 (e.g. MEF-1 strain), and poliovirus Type 3 (e.g. Saukett strain). A typical amount of poliovirus per dose is 40 DU ("D-antigen unit") for Type 1, 8 DU for Type 2, and 32 DU for Type 3, although lower doses can be used with the invention due to the antigen-sparing nature of the adjuvants.

The immunogen may elicit an immune response against a cytomegalovirus ("CMV"). For example, the immunogen may be a recombinant glycoprotein B e.g. the soluble antigen used in reference 36.

The immunogen may elicit an immune response against a human immunodeficiency virus e.g. against HIV-1 or HIV-2. For example, the immunogen may be a HIV envelope glycoprotein. For instance, engineered envelope glycoproteins are available, such as gp140, which can form oligomers (referred to as "o-gp140"). The gp140 polypeptide includes the gp120 sequence and the ectodomain of gp41 [37], and has been reported to be a better immunogen than gp120 [38]. Thus a useful envelope glycoprotein may include a portion of gp41 but not include its transmembrane domain. The gp140 form of the envelope glycoprotein can have its V2 loop deleted, to give gp140ΔV2 mutants, and such delections have been reported to improve immunogenicity. The ΔV2 mutants of gp140 have been shown to form trimers [39].

The immunogen may elicit an immune response against rabies virus. A suitable immunogen is an inactivated rabies virus (ref. 40, RabAvert™).

The immunogen may elicit an immune response against a human papillomavirus. Useful immunogens are L1 capsid proteins, which can assemble to form structures known as virus-like particles (VLPs). The VLPs can be produced by recombinant expression of L1 in yeast cells (e.g. in *S. cerevisiae*) or in insect cells (e.g. in *Spodoptera* cells, such as *S. frugiperda*, or in *Drosophila* cells). For yeast cells, plasmid vectors can carry the L1 gene(s); for insect cells, baculovirus vectors can carry the L1 gene(s). More preferably, the composition includes L1 VLPs from both HPV-16 and HPV-18 strains. This bivalent combination has been shown to be highly effective [41]. In addition to HPV-16 and HPV-18 strains, it is also possible to include L1 VLPs from HPV-6 and HPV-11 strains.

The immunogen may elicit an immune response against a tumour antigen, such as MAGE-1, MAGE-2, MAGE-3 (MAGE-A3), MART-1/Melan A, tyrosinase, gp100, TRP-2, etc. The immunogen may elicit an immunotherapeutic response against lung cancer, melanoma, breast cancer, prostate cancer, etc.

The immunogen may elicit an immune response against a hapten conjugated to a carrier protein, where the hapten is a drug of abuse [42]. Examples include, but are not limited to, opiates, marijuana, amphetamines, cocaine, barbituates, glutethimide, methyprylon, chloral hydrate, methaqualone, benzodiazepines, LSD, nicotine, anticholinergic drugs, antipsychotic drugs, tryptamine, other psychomimetic drugs, sedatives, phencyclidine, psilocybine, volatile nitrite, and other drugs inducing physical and/or psychological dependence.

Various other immunogens may be used.

Compositions for Immunisation Against *Neisseria meningitidis*

The invention is particularly useful for immunising against meningococcus e.g. against serogroup B.

Preferred immunogenic compositions of the invention comprise: (i) an aluminium hydroxide adjuvant; (ii) an arginine salt of the compound of formula (I) described herein; and (iii) a polypeptide comprising SEQ ID NO: 1; wherein the compound of formula (I) described herein of the arginine salt of (ii) is adsorbed to the aluminium hydroxide.

Preferred immunogenic compositions of the invention comprise: (i) an aluminium hydroxide adjuvant; (ii) an arginine salt of the compound of formula (I) described herein; and (iii) a polypeptide comprising SEQ ID NO: 2; wherein the compound of formula (I) described herein of the arginine salt of (ii) is adsorbed to the aluminium hydroxide.

Preferred immunogenic compositions of the invention comprise: (i) an aluminium hydroxide adjuvant; (ii) an arginine salt of the compound of formula (I) described herein; (iii) a first polypeptide comprising SEQ ID NO: 1; and (iv) a second polypeptide comprising SEQ ID NO: 2; wherein the compound of formula (I) described herein of the arginine salt of (ii) is adsorbed to the aluminium hydroxide. This composition can include further polypeptide(s) e.g. comprising any of SEQ ID NOs: 3, 4 or 5.

Preferred immunogenic compositions of the invention comprise: (i) an aluminium hydroxide adjuvant; (ii) an arginine salt of the compound of formula (I) described herein; (iii) a first polypeptide comprising SEQ ID NO: 1; (iv) a second polypeptide comprising SEQ ID NO: 2; and (v) a third polypeptide comprising SEQ ID NO: 3; wherein the compound of formula (I) described herein of the arginine salt of (ii) is adsorbed to the aluminium hydroxide.

Preferred immunogenic compositions of the invention comprise: (i) an aluminium hydroxide adjuvant; (ii) an arginine salt of the compound of formula (I) described herein; (iii) a first polypeptide comprising SEQ ID NO: 1; (iv) a second polypeptide comprising SEQ ID NO: 2; and (v) a third polypeptide comprising SEQ ID NO: 4; wherein the arginine salt of (ii) is adsorbed to the aluminium hydroxide. SEQ ID NO: 4 is SEQ ID NO: 126 from reference 43.

Preferred immunogenic compositions of the invention comprise: (i) an aluminium hydroxide adjuvant; (ii) an arginine salt of the compound of formula (I) described herein; (iii) a first polypeptide comprising SEQ ID NO: 1; (iv) a second polypeptide comprising SEQ ID NO: 2; and (v) a third polypeptide comprising SEQ ID NO: 5; wherein the compound of formula (I) described herein of the arginine salt of (ii) is adsorbed to the aluminium hydroxide.

Any of the first, second and/or third polypeptides can differ from the relevant SEQ ID NO: 1, 2, 3, 4 or 5 by up to 3 amino acids, provided that the polypeptide can still elicit antibodies which bind to a polypeptide which consists of SEQ ID NO: 1, 2, 3, 4 or 5, as appropriate.

Ideally, 1 2 or 3 of the first second and/or third polypeptides is/are also adsorbed to the aluminium hydroxide. These polypeptides are disclosed in more detail in references 12, 44 and 45. The composition may include 5-100 µg of each polypeptide. The composition ideally does not include any bacterial outer membrane vesicles.

The composition may include from 5-100 µg of an arginine salt of the compound of formula (I).

The composition may include a histidine buffer e.g. a 10 mM histidine buffer. It may include sucrose and/or sodium chloride. It may be administered in a dosage volume of 0.5 ml e.g. for intramuscular injection.

Further immunogenic compositions of the invention may comprise: (i) an aluminium hydroxide adjuvant; (ii) an arginine salt of the compound of formula (I) described herein; (iii) a meningococcal factor H binding protein antigen, provided that this antigen is not a fusion protein having an amino acid sequence comprising SEQ ID NO: 8 from reference 46. The factor H binding protein antigen can be adsorbed to the aluminium hydroxide too.

Compositions with Multiple Different Immunogens

According to a further aspect, the invention provides a composition comprising an adjuvant complex of the invention in combination with at least two different immunogens.

The invention also provides a kit comprising (i) an adjuvant complex in a first container and (ii) at least one immunogen in a second container. The first container can optionally include at least one immunogen in addition to the complex.

The immunogenic compound in the adjuvant complex can be any arginine salt of the compound of formula (I) as disclosed herein.

The "at least two different immunogens" in some embodiments does not consist of: (i) a combination of a measles virus immunogen, a mumps virus immunogen, and a rubella virus immunogen; (ii) a combination of a measles virus immunogen, a mumps virus immunogen, a rubella virus immunogen, and a varicella virus immunogen; (iii) a diphtheria vaccine, a tetanus vaccine, and a pertussis vaccine; (iv) a tetravalent combination of conjugates from meningococcus serogroups A, C, W135 and Y; (v) a combination of bacterial antigens from serogroups A, B, C, W135 and/or Y of *N. meningitidis*; (vi) a combination including antigens from two or more different strains of influenza viruses; (vii) a combination of outer-membrane vesicles from serogroups A, C, W135, Y, X and/or B of *N. meningitidis*; (viii) a combination of saccharides from different pneumococcal serotypes; (ix) a combination of *Moraxella catarrhalis* antigens; (x) a combination of *Bordetella pertussis* holotoxin, filamentous haemagglutinin, pertactin and/or agglutinogens 2 and 3; (xi) a combination of multiple different polypeptide antigens from *N. meningitidis*.

The "at least two different immunogens" in some embodiments does not consist of a combination of multiple different polypeptide antigens from *N. meningitidis* such as the combination disclosed in references 12 and 46.

The "at least two different immunogens" can include at least one bacterial antigen and at least one viral antigen.

If the "at least two different immunogens" include only bacterial immunogens then they ideally include immunogens for at least two different species of bacteria (thus, for instance, excluding a combination of different meningococcal capsular saccharides, as these are all from a single species).

The "at least two different immunogens" should not be conjugated to each other. Thus a conjugate of a Hib saccharide and a tetanus toxoid is not "at least two different immunogens" as used herein.

Preferred embodiments of "at least two different immunogens" include compositions, such as: (i) a diphtheria toxoid, a tetanus toxoid, and an acellular pertussis antigen e.g. comprising a pertussis toxoid, filamentous hemagglutinin and/or pertactin; (ii) a diphtheria toxoid, a tetanus toxoid, a pertussis antigen, and a *H. influenzae* type B capsular saccharide conjugate; (iii) a diphtheria toxoid, a tetanus toxoid, a pertussis antigen, and a hepatitis B virus surface antigen; (iv) a diphtheria toxoid, a tetanus toxoid, a pertussis antigen, a hepatitis B virus surface antigen and a *H. influenzae* type B capsular saccharide conjugate; (v) a diphtheria toxoid, a tetanus toxoid, a pertussis antigen, and an inactivated poliovirus antigen; (vi) a diphtheria toxoid, a tetanus toxoid, a pertussis antigen, a *H. influenzae* type B capsular saccharide conjugate, a hepatitis B virus surface antigen, and an inactivated poliovirus antigen; or (vii) a hepatitis A virus antigen and a hepatitis B virus antigen.

Where a composition includes an inactivated poliovirus antigen it preferably includes antigens from each of poliovirus Type 1 (e.g. Mahoney strain), poliovirus Type 2 (e.g. MEF-1 strain), and poliovirus Type 3 (e.g. Saukett strain).

Where a composition includes a pertussis antigen it ideally does not include whole inactivated *B. pertussis* cells i.e. it is ideally an acellular vaccine.

As well as including D, T, Pa, HBsAg, Hib and/or poliovirus antigens, a composition of the invention may include further antigens e.g. from further pathogens. For example, these antigens may be from *N. meningitidis* (one or more of serogroups A, B, C, W135 and/or Y) or *S. pneumoniae*. Thus a composition may include two or three of: (i) one or more of D, T, Pa, HBsAg, Hib and/or poliovirus antigens; (ii) a conjugated capsular saccharide from one or more of meningococcal serogroups A, C, W135 and/or Y; (iii) a polypeptide antigen from meningococcus, such as a fHbp.

Compositions of the invention which include multiple immunogens preferably do not include any bacterial outer membrane vesicles.

In Situ Precipitation Processes

According to one aspect, the invention provides a process for preparing an adjuvant complex, comprising steps of (i) preparing an aqueous mixture of an arginine salt of the compound of formula (I) as described herein and a soluble aluminium salt; then (ii) adding a non-aluminium salt to the aqueous mixture in order to form a precipitated aluminium salt to which the compound of formula (I) as described herein is adsorbed.

According to another aspect, the invention provides a process for preparing an immunogenic composition, comprising a step of mixing (i) an aqueous mixture an arginine salt of the compound of formula (I) as described herein and a soluble aluminium salt with (ii) a buffered aqueous mixture of an immunogen, wherein the mixing step causes precipitation of an aluminium salt to which the compound of formula (I) as described herein and the immunogen are adsorbed.

The invention also provides a process for preparing an immunogenic composition, comprising a step of mixing (i) an aqueous solution of a soluble aluminium salt with (ii) a buffered aqueous mixture of an immunogen and an arginine salt of the compound of formula (I) as described herein, wherein the mixing step causes precipitation of an aluminium salt to which the compound of formula (I) as described herein and the immunogen are adsorbed.

The invention also provides a process for preparing an immunogenic composition, comprising a step of mixing (i) an aqueous solution of a soluble aluminium salt and an immunogen with (ii) a buffered aqueous mixture of an arginine salt of the compound of formula (I) as described herein, wherein the mixing step causes precipitation of an aluminium salt to which the compound of formula (I) as described herein and the immunogen are adsorbed.

The invention also provides immunogenic compositions obtained or obtainable by these processes.

In these processes the soluble aluminium salt will typically be alum ($KAl(SO_4)_2$, typically as $KAl(SO_4)_2.12H_2O$) or aluminium chloride. Adding an alternative anion to this soluble salt can cause an aluminium salt adjuvant to precipitate in situ.

The alternative anion is typically added as part of a buffer. Thus, for instance, if a phosphate buffer is added to the soluble aluminium salt then an aluminium phosphate adjuvant can precipitate. The buffer will typically be an acetate, carbonate, or phosphate buffer. Addition of the buffer to an alum solution leads to precipitation of an amorphous aluminium hydroxy(buffer anion)sulfate e.g. aluminium hydroxyphosphatesulfate (see chapter 9 of reference 4).

Pharmaceutical Compositions and Products

The invention provides a pharmaceutical composition comprising an arginine salt of the compound of formula (I) as described herein. This composition can also include an insoluble metal salt and/or an immunogen.

The invention also provides a pharmaceutical composition comprising an arginine salt of the compound of formula (I) as described herein and an insoluble metal salt. This composition can also include an immunogen.

The invention also provides an immunogenic pharmaceutical composition comprising an arginine salt of the compound of formula (I) as described herein and an immunogen. This composition can also include an insoluble metal salt.

The invention also provides a method for preparing a pharmaceutical composition, comprising a step of combining a an arginine salt of the compound of formula (I) as described herein with one or more pharmaceutically acceptable excipients.

Pharmaceutical compositions usually include components in addition to the arginine salt of the compound of formula (I) as described herein, insoluble metal salt and/or immunogen e.g. they typically include one or more pharmaceutical carrier(s) and/or excipient(s). A thorough discussion of such components is available in reference 47.

Pharmaceutical compositions are preferably in aqueous form, particularly at the point of administration, but they can also be presented in non-aqueous liquid forms or in dried forms e.g. as gelatin capsules, or as lyophilisates, etc.

Pharmaceutical compositions may include one or more preservatives, such as thiomersal or 2-phenoxyethanol. Mercury-free compositions are preferred, and preservative-free vaccines can be prepared.

Pharmaceutical compositions can include a physiological salt, such as a sodium salt e.g. to control tonicity. Sodium chloride (NaCl) is typical, which may be present at between 1 and 20 mg/ml e.g. 10±2 mg/ml or 9 mg/ml. Other salts that may be present include potassium chloride, potassium dihydrogen phosphate, disodium phosphate dehydrate, magnesium chloride, calcium chloride, etc.

Pharmaceutical compositions can have an osmolality of between 200 mOsm/kg and 400 mOsm/kg, e.g. between 240-360 mOsm/kg, or between 290-310 mOsm/kg.

Pharmaceutical compositions may include compounds (with or without an insoluble metal salt) in plain water (e.g. w.f.i.) but will usually include one or more buffers. Typical buffers include: a phosphate buffer (except in the fifteenth aspect); a Tris buffer; a borate buffer; a succinate buffer; a histidine buffer (particularly with an aluminum hydroxide adjuvant); or a citrate buffer. Buffer salts will typically be included in the 5-20 mM range.

Pharmaceutical compositions typically have a pH between 5.0 and 9.5 e.g. between 6.0 and 8.0.

Pharmaceutical compositions are preferably sterile.

Pharmaceutical compositions preferably non-pyrogenic e.g. containing <1 EU (endotoxin unit, a standard measure) per dose, and preferably <0.1 EU per dose.

Pharmaceutical compositions are preferably gluten free.

Pharmaceutical compositions are suitable for administration to animal (and, in particular, human) patients, and thus include both human and veterinary uses. They may be used in a method of raising an immune response in a patient, comprising the step of administering the composition to the patient.

Pharmaceutical compositions may be prepared in unit dose form. In some embodiments a unit dose may have a volume of between 0.1-1.0 ml e.g. about 0.5 ml.

The invention also provides a delivery device (e.g. syringe, nebuliser, sprayer, inhaler, dermal patch, etc.) containing a pharmaceutical composition of the invention e.g. containing a unit dose. This device can be used to administer the composition to a vertebrate subject.

The invention also provides a sterile container (e.g. a vial) containing a pharmaceutical composition of the invention e.g. containing a unit dose.

The invention also provides a unit dose of a pharmaceutical composition of the invention.

The invention also provides a hermetically sealed container containing a pharmaceutical composition of the invention. Suitable containers include e.g. a vial.

The invention also provides a kit comprising first and second kit components, wherein: (i) the first kit component comprises an insoluble metal salt and an immunogen; and (ii) the second kit component comprises an arginine salt of the compound of formula (I) as described herein. The second component ideally does not include an insoluble metal salt and/or does not include an immunogen. The first and second components can be combined to provide a composition suitable for administration to a subject.

The invention also provides a kit comprising first and second kit components, wherein: (i) the first kit component comprises an insoluble metal salt and an arginine salt of the compound of formula (I) as described herein; and (ii) the second kit component comprises an immunogen. The second component ideally does not include an insoluble metal salt and/or a TLR agonist. In some embodiments, the second component is lyophilised. The first and second components can be combined to provide a pharmaceutical composition suitable for administration to a subject.

The invention also provides a kit comprising first and second kit components, wherein: (i) the first kit component comprises an immunogen and an arginine salt of the compound of formula (I) as described herein; and (ii) the second kit component comprises an insoluble metal salt. The second component ideally does not include an immunogen and/or a TLR agonist. The first and second components can be combined to provide a pharmaceutical composition suitable for administration to a subject.

In some embodiments these kits comprise two vials. In other embodiments they comprise one ready-filled syringe and one vial, with the contents of the syringe being mixed with the contents of the vial prior to injection. A syringe/vial arrangement is useful where the vial's contents are lyophilised. Usually, though, the first and second kit components will both be in aqueous liquid form.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. by an inhaler, using a fine powder or a spray. The composition may be prepared as a suppository or pessary. The composition may be prepared for nasal, aural or ocular administration e.g. as a spray or drops. The composition may be in kit form, designed such that a combined composition is reconstituted just prior to administration to a patient. Such kits may comprise one or more antigens in liquid form and one or more lyophilised antigens. Injectables for intramuscular administration are typical.

Compositions comprise an effective amount of an arginine salt of the compound of formula (I) i.e. an amount which, when administered to an individual, either in a single dose or as part of a series, is effective for enhancing the immune response to a co-administered immunogen. This amount can vary depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. The amount will fall in a relatively broad range that can be determined through routine trials. An amount of up to 2.5 mg per dose can be used, for example from 1-1000 μg/dose or from 10-100 μg per dose.

Methods of Treatment, and Administration of Immunogenic Compositions

The invention provides a method of raising an immune response in a subject, comprising the step of administering to the subject an arginine salt of the compound of formula (I) as described herein, complex and/or composition of the invention.

The invention also provides an arginine salt of the compound of formula (I) as described herein, complex and/or composition of the invention, for use in a method of raising an immune response in a subject.

The invention also provides the use of an arginine salt of the compound of formula (I) as described herein or complex of the invention in the manufacture of a medicament for raising an immune response in a subject.

The invention also provides the use of (i) an arginine salt of the compound of formula (I) as described herein and (ii) an insoluble metal salt in the manufacture of a medicament for raising an immune response in a subject. Similarly, the invention also provides the use of (i) an arginine salt of the compound of formula (I) as described herein (ii) an insoluble metal salt and (iii) an immunogen in the manufacture of a medicament (e.g. a vaccine) for raising an immune response in a subject.

The invention is suitable for raising immune responses in human or non-human animal (in particular mammal) subjects. Compositions prepared according to the invention may be used to treat both children and adults.

The immune response stimulated by these methods and uses will generally include an antibody response, preferably a protective antibody response. Methods for assessing antibody responses after immunisation are well known in the art. For example, the immune response can include an increase in IFN-γ, IL-10, IL-12, MCP-1, mKC and/or TNF-α.

Treatment can be by a single dose schedule or a multiple dose schedule. Multiple doses may be used in a primary immunisation schedule and/or in a booster immunisation schedule. Administration of more than one dose (typically two doses) is particularly useful in immunologically naïve patients. Multiple doses will typically be administered at least 1 week apart (e.g. about 2 weeks, about 3 weeks, about 4 weeks, about 6 weeks, about 8 weeks, about 10 weeks, about 12 weeks, etc.).

The invention also relates to compounds of formula (Ia) shown below.

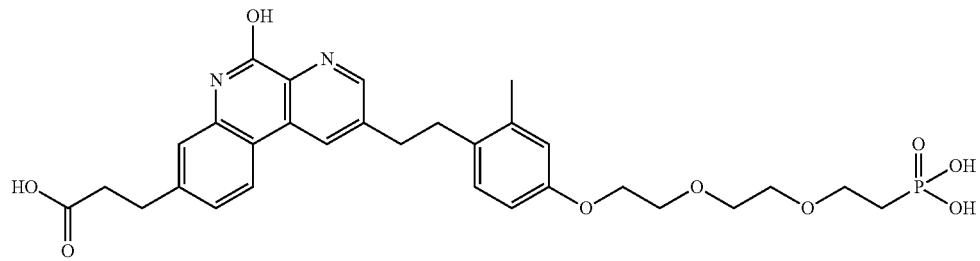 [SMILES: Cc1cc(OCCOCCOCCP(=O)(O)O)ccc1CCc1cnc2c(O)nc3cc(CCC(=O)O)ccc3c2c1]

Formula (Ia)

and salts or solvates thereof. The salts of the compounds of formula (Ia) include arginine salts, and L-arginine salts in particular.

General

The term "comprising" encompasses "including" as well as "consisting" and "consisting essentially of" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

The skilled person will appreciate that the compounds of formula I can exist as tautomers (e.g. the benzonaphthyridine ring can tautomerise). The present invention comprehends the different tautomeric forms in isolation from each other as well as mixtures of these tautomers. The preparation of salt forms of the free base can change the balance of tautomers relative to the free base.

Phosphorous-containing groups employed with the invention may exist in a number of protonated and deprotonated forms depending on the pH of the surrounding environment, for example the pH of the solvent in which they are dissolved. Therefore, although a particular form may be illustrated it is intended, unless otherwise mentioned, for these illustrations to merely be representative and not limiting to a specific protonated or deprotonated form. For example, in the case of a phosphate group, this has been illustrated as —OP(O)(OH)$_2$ but the definition includes the protonated forms —[OP(O)(OH$_2$)(OH)]$^+$ and —[OP(O)(OH$_2$)$_2$]$^{2+}$, and the deprotonated forms —[OP(O)(OH)(O)]$^-$ and [OP(O)(O)$_2$]$^{2-}$ e.g. that may exist at different pH values.

MODES FOR CARRYING OUT THE INVENTION

Free Base Synthesis

Figure 1:
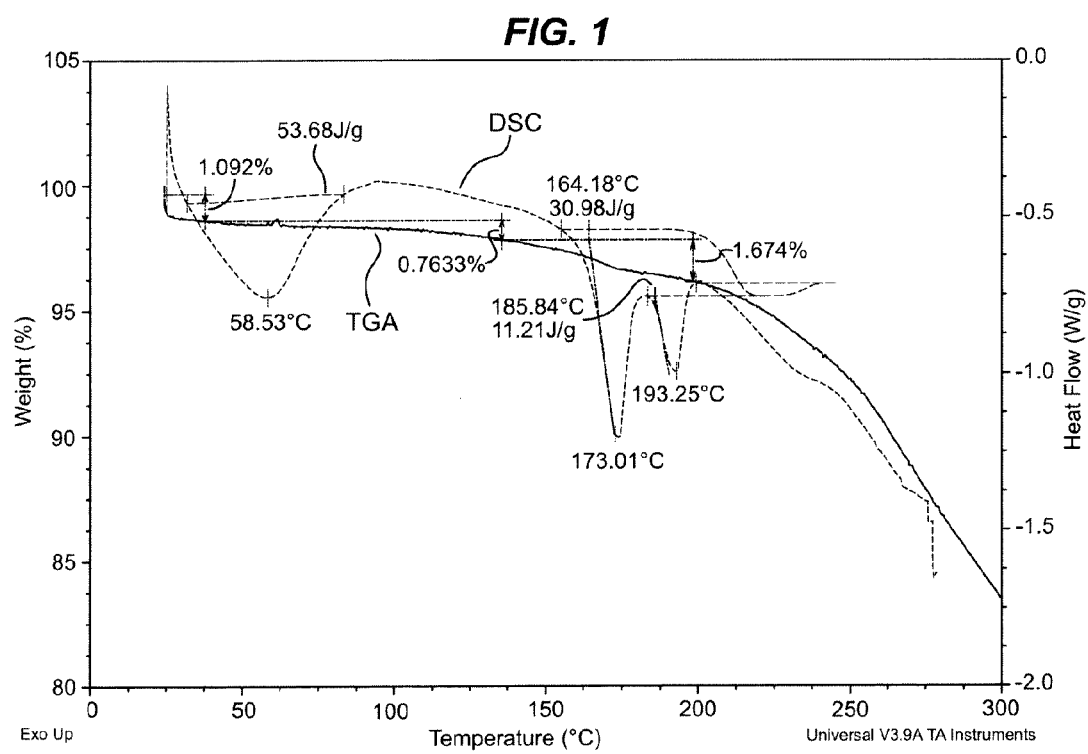
FIG. 1 shows a TGA and DSC analysis for a L-arginine salt of the compound of formula (I).

Synthesis of 3-(5-amino-2-(2-methyl-4-(2-(2-(2-phosphonoethoxy)ethoxy)ethoxy)phenethyl)benzo[f][1,7]naphthyridin-8-yl)propanoic acid free base is described below, with reference to scheme 1.

Step 1: (E)-ethyl 3-(3-(tert-butoxycarbonylamino)-4-chlorophenyl)acrylate (3)

To a solution of tert-butyl 5-bromo-2-chlorophenylcarbamate (1) (1.0 equiv.) in acetonitrile (0.3M) and EtOH (0.5M) was added K$_2$CO$_3$ (2.0 equiv.). The reaction was degassed and flushed with N$_2$, then added (E)-ethyl 3-(4,4,5,5-tetramethyl-1,3,2-dioxaborolan-2-yl)acrylate (2) (1.2 equiv.) and Pd(PPh$_3$)$_4$ (0.1 equiv.). The reaction was flushed again with N$_2$ and stirred at 100° C. overnight. After cooling to room temperature, hexane was added, and the mixture was filtered through a pad of silica, eluting with EA/Hex (1:1) until the product was completely eluted. The filtrate was concentrated and purified on Combiflash, eluting with 0-15% EA in Hex to give (E)-ethyl 3-(3-(tert-butoxycarbonylamino)-4-chlorophenyl)acrylate (3) as a white solid.

Scheme 1
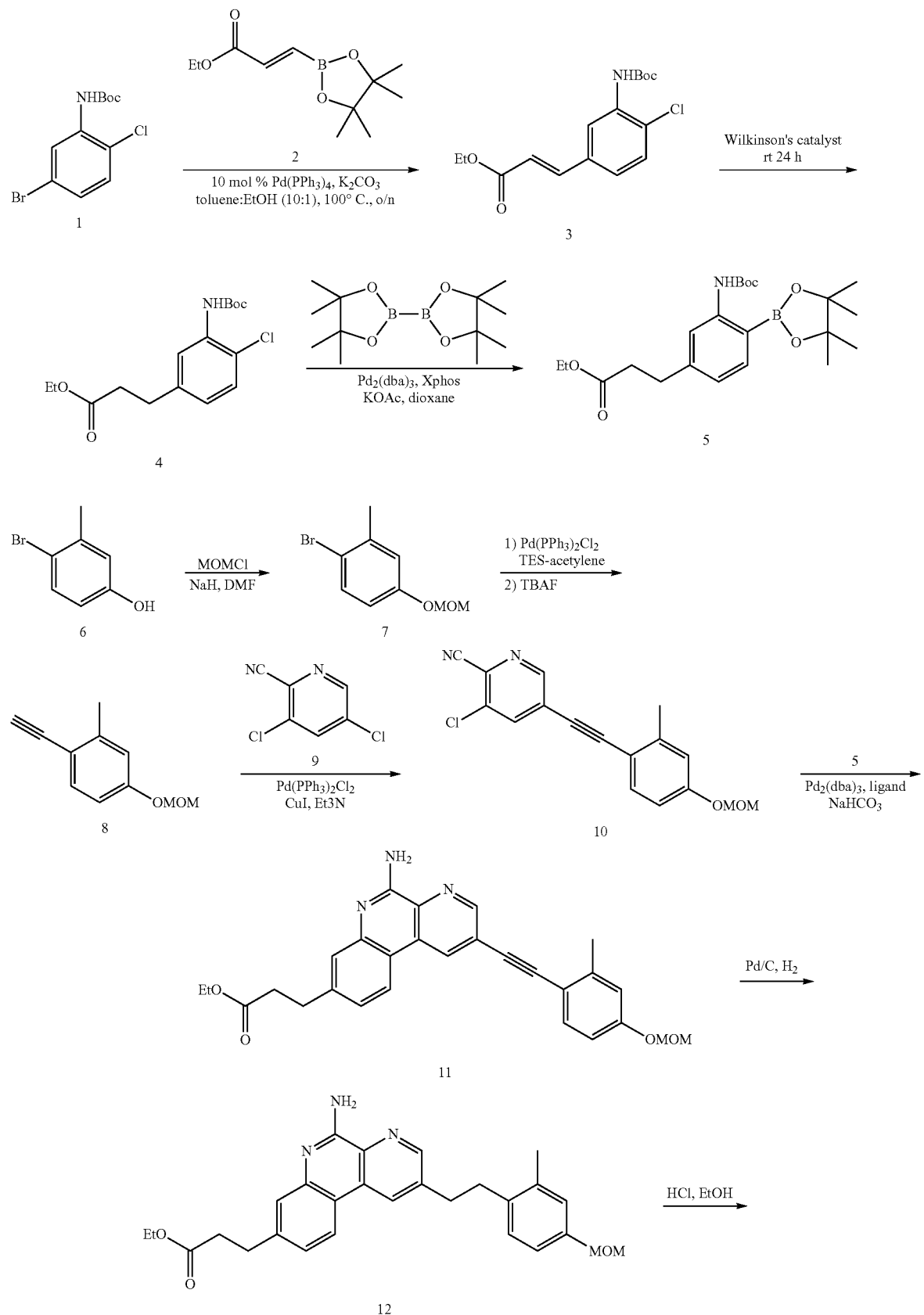

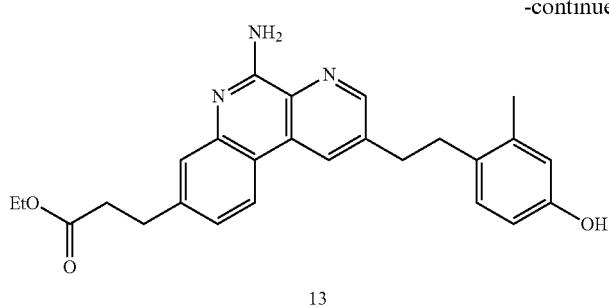
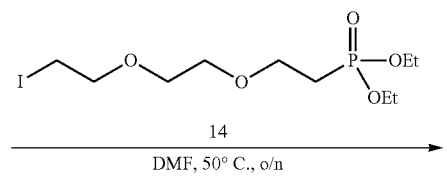
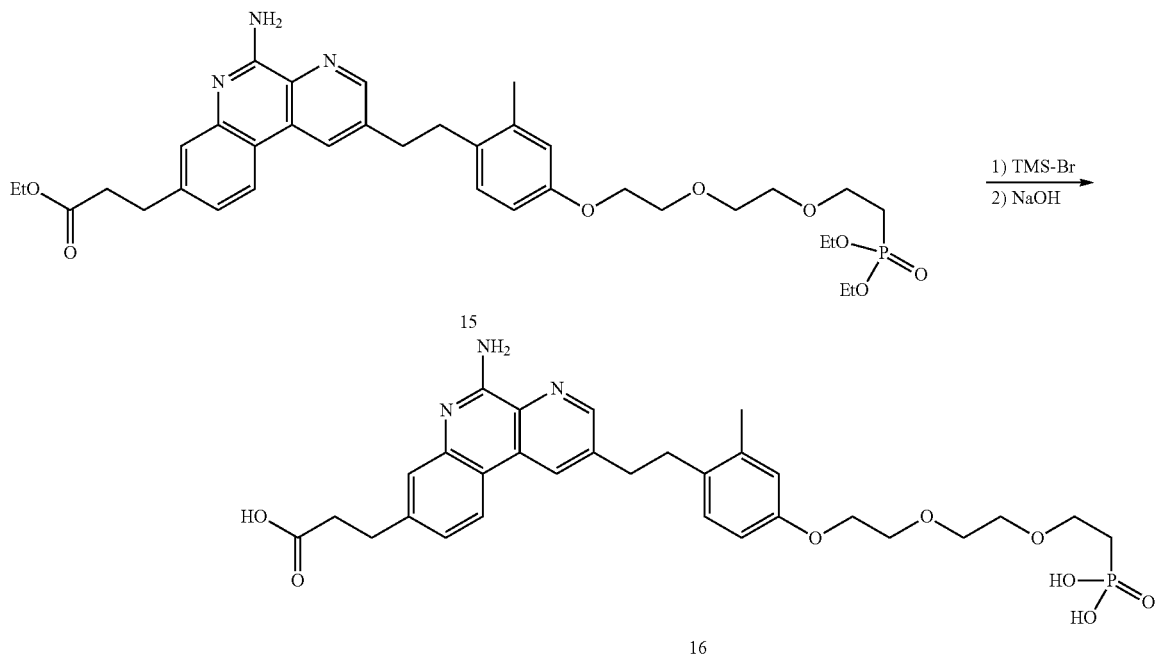

Step 2: ethyl 3-(3-(tert-butoxycarbonylamino)-4-chlorophenyl)propanoate (4)

To a solution of (E)-ethyl 3-(3-(tert-butoxycarbonylamino)-4-chlorophenyl)acrylate (3) (1.0 equiv.) in ethyl acetate/ethanol (1:1, 0.3M) was added Wilkinson's catalyst (0.10 equiv.). Hydrogen gas was introduced via a balloon, and the reaction was stirred at room temperature for 24 hours. The mixture was filtered through a pad of celite, washing with dichloromethane. The filtrate was concentrated in vacuo and purified by Combiflash using 0-10% ethyl acetate in hexane to give ethyl 3-(3-(tert-butoxycarbonylamino)-4-chlorophenyl)propanoate (4) as a solid.

Step 3: ethyl 3-(3-(tert-butoxycarbonylamino)-4-(4,4,5,5-tetramethyl-1,3,2-dioxaborolan-2-yl)phenyl)propanoate (5)

A solution of ethyl 3-(3-(tert-butoxycarbonylamino)-4-chlorophenyl)propanoate (4) (1.0 equiv.), 4,4,4',4',5,5,5',5'-octamethyl-2,2'-bi(1,3,2-dioxaborolane) (2.0 equiv.), tris(dibenzylideneacetone)dipalladium(0) (0.05 equiv.), 2-dicyclohexylphosphino-2',4',6'-triisopropylbiphenyl (0.20 equiv.), and potassium acetate (2.0 equiv.) in 1,4-dioxane (0.2M) was degassed and stirred at 100° C. overnight. After cooling to ambient temperature, the reaction content was concentrated in vacuo. The crude material was purified by Combiflash using 0-50% ethyl acetate in hexane to afford ethyl 3-(3-(tert-butoxycarbonylamino)-4-(4,4,5,5-tetramethyl-1,3,2-dioxaborolan-2-yl)phenyl)propanoate (5) as a brown oil. The product was stored at −20° C. and used within a month of synthesis.

Step 4: 1-bromo-4-(methoxymethoxy)-2-methylbenzene (7)

To a solution of 4-bromo-3-methylphenol (6) (1.0 equiv.) in DMF (0.5 M) at 0° C. was added portionwise 60% wt NaH (1.5 equiv.). The addition was controlled such that internal reaction temperature never went above 10° C. The reaction was stirred at room temperature for 45 minutes, then a solution of chloro(methoxy)methane (1.2 equiv.) in DMF (3M) was added dropwise via additional funnel. The reaction was stirred at room temperature for 3.5 hours, and then quenched by pouring into ice. The resulting mixture was stirred at room temperature for 1 hour. Ether was added, and the two layers were separated. The aqueous layer was extracted (1×) with ether. The combined organic layers were washed with water (2×), brine, dried over MgSO$_4$, and concentrated to give 1-bromo-4-(methoxymethoxy)-2-methylbenzene (7) as a colorless oil. The crude material was used in the next step without further purification.

Step 5: triethyl((4-(methoxymethoxy)-2-methylphenyl)ethynyl)silane

A solution of 1-bromo-4-(methoxymethoxy)-2-methylbenzene (1.0 equiv.), triethylamine (5.0 equiv.) in DMF (0.5M) was degassed and flushed with nitrogen. To the reaction was added TES-acetylene (1.05 equiv.), CuI (0.098 equiv.), and Pd(PPh$_3$)$_2$Cl$_2$ (0.098 equiv.). The reaction was heated to 60° C. and stirred overnight. After cooling to room temperature, water and ether were added. The layers were separated, and the organic layer was washed with water (2×). The organic layer was separated and passed through a pad of silica (packed with hexane). The silica was eluted with 10% EA in Hex.

The fractions were combined and concentrated to give triethyl((4-(methoxymethoxy)-2-methylphenyl)ethynyl)silane as a black oil. The crude material was used in the next step without further purification.

Step 6: 1-ethynyl-4-(methoxymethoxy)-2-methylbenzene (8)

To a solution of triethyl((4-(methoxymethoxy)-2-methylphenyl)ethynyl)silane (1.0 equiv.) at 0° C. was slowly added tetrabutylammonium fluoride (1M solution in THF, 0.20 equiv.). At this point, the ice-bath was removed and the reaction mixture was allowed to stir at room temperature for 45 minutes. The reaction mixture was then passed through a pad of silica (packed with hexane) and eluted with 20% EtOAc in Hexanes to remove insoluble salts. The crude product was then purified by Combiflash using 0-10% EtOAc in Hexanes to give 1-ethynyl-4-(methoxymethoxy)-2-methylbenzene (8) as a slightly brown liquid.

Step 7: 3-chloro-5-((4-(methoxymethoxy)-2-methylphenyl)ethynyl)picolinonitrile (10)

A solution of 1-ethynyl-4-(methoxymethoxy)-2-methylbenzene (8) (1.0 equiv.), 3,5-dichloropicolinonitrile (9) (0.90 equiv.), CuI (0.10 equiv.), and Pd(PPh$_3$)$_2$Cl$_2$ (0.10 equiv.), and triethylamine (5.0 equiv.) in DMF (0.25M) was degassed and flushed with nitrogen. The reaction mixture was then heated to 60° C. and stirred overnight. After cooling to room temperature, water was added. The mixture was extracted with EA (2×). The combined organic layers were washed with 10% aq NH$_4$OH (2×), brine, and concentrated. The crude material was filtered through a pad of silica (wetted with hexane). The silica was eluted with 10% EA in Hex. The fractions were combined and concentrated. The resulting solids were washed in hot ether and filtered to give a yellow solid, which was used in the next step without further purification. The filtrate was concentrated and purified by Combiflash using 0-10% EtOAc in Hexanes to give 3-chloro-5-((4-(methoxymethoxy)-2-methylphenyl)ethynyl)picolinonitrile (10) as a yellow solid.

Step 8: ethyl 3-(5-amino-2-((4-(methoxymethoxy)-2-methylphenyl)ethynyl)-benzo[f][1,7]naphthyridin-8-yl)propanoate (11)

A solution of 3-chloro-5-((4-(methoxymethoxy)-2-methylphenyl)ethynyl)picolinonitrile (10) (1.0 equiv.), ethyl 3-(3-(tert-butoxycarbonylamino)-4-(4,4,5,5-tetramethyl-1,3,2-dioxaborolan-2-yl)phenyl)propanoate (5) (1.25 equiv.), tris(dibenzylideneacetone)dipalladium(0) (0.10 equiv.), dicyclohexyl(2',6'-dimethoxybiphenyl-2-yl)phosphine (0.20 equiv.), and sodium bicarbonate (3.0 equiv.) in n-butanol/H$_2$O (5:1, 0.2M) was degassed and stirred at 100° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated in vacuo. The crude material was purified by flash chromatography on a COMBIFLASH® system (ISCO) using 0-40% ethyl acetate in DCM first to remove the impurity, then 0-4% MeOH in DCM to give ethyl 3-(5-amino-2-((4-(methoxymethoxy)-2-methylphenyl)ethynyl)-benzo[f][1,7]naphthyridin-8-yl)propanoate (11). Further purification was accomplished by precipitating and washing in hot ether.

Step 9: ethyl 3-(5-amino-2-(4-(methoxymethoxy)-2-methylphenethyl)benzo[f][1,7]naphthyridin-8-yl)propanoate (12)

A solution of ethyl 3-(5-amino-2-((4-(methoxymethoxy)-2-methylphenyl)ethynyl)-benzo[f][1,7]naphthyridin-8-yl)propanoate (11) (1.0 equiv.) in EtOH/THF (3:1, 0.16M) was flushed with nitrogen. Then, 10% wt Pd/C (0.20 equiv. by weight) was added. The reaction was flushed with hydrogen (2×) and stirred under a hydrogen balloon. After 24 hours, the reaction was filtered through a pad of celite, washing with 5% MeOH in DCM. The filtrate was checked for the presence of starting material using LCMS. The hydrogenation reaction was repeated until no more of the alkyne starting material or alkene intermediate was detected. The crude product was purified by Combiflash using 0-4% MeOH in DCM to give ethyl 3-(5-amino-2-(4-(methoxymethoxy)-2-methylphenethyl)benzo[f][1,7]naphthyridin-8-yl)propanoate (12) as a white solid.

Step 10: ethyl 3-(5-amino-2-(4-hydroxy-2-methylphenethyl)benzo[f][1,7]naphthyridin-8-yl)propanoate (13)

Ethyl 3-(5-amino-2-(4-(methoxymethoxy)-2-methylphenethyl)benzo[f][1,7]naphthyridin-8-yl)propanoate (12) (1.0 equiv.) was dissolved in EtOH (0.2M), then added a solution of 4M HCl in dioxane (0.2M). The product precipitated out as a yellow salt. After stirring for 3 hours, the reaction was poured into a stirring solution of ether. The mixture was stirred for 10 minutes, then filtered and washed with ether. Ethyl 3-(5-amino-2-(4-hydroxy-2-methylphenethyl)benzo[f][1,7]naphthyridin-8-yl)propanoate (13) was obtained as a yellow solid which was dried on vacuum overnight (bis-HCl salt). Alternatively, the crude product was purified by Combiflash using 0-5% MeOH in DCM to give the free base.

Step 11: diethyl 2-(2-(2-iodoethoxy)ethoxy)ethylphosphonate

A microwave tube was charged with a stirring bar, commercially available 1,2-bis(2-iodoethoxy)ethane (1.0 equiv.) and triethylphosphite (1.0 equiv.). The microwave tube was capped and then irradiated at 160° C. for 40 minutes with stirring. The reaction mixture was cooled down to room temperature and was purified by Combiflash using 0-75% EtOAc in hexanes, or alternatively by RP-HPLC (0.035% TFA in ACN:0.05% TFA in H$_2$O, C18 column), to give diethyl 2-(2-(2-iodoethoxy)ethoxy)ethylphosphonate as pale yellow oil.

Step 12: ethyl 3-(5-amino-2-{2-[4-(2-{2-[2-(diethoxyphosphoryl)ethoxy]ethoxy}ethoxy)-2-methylphenyl]ethyl}benzo[f]1,7-naphthyridin-8-yl)propanoate (15)

To a solution of ethyl 3-(5-amino-2-(4-hydroxy-2-methylphenethyl)benzo[f][1,7]naphthyridin-8-yl)propanoate (13) (1.0 equiv.) dissolved in DMF (0.14M) was added a solution of diethyl 2-(2-(2-iodoethoxy)ethoxy)ethylphosphonate (14): from step 11 above (1.3 equiv.) in DMF (0.7M) and cesium carbonate (4 equiv.). The reaction was stirred at 60° C. After 1.5 hours (or until reaction is complete by LCMS), DCM (2 volume equivalent) was added to the reaction. The solids (inorganic) were filtered, and the filtrate was concentration. The crude product was purified by Combiflash using 0-5% MeOH in DCM to give ethyl 3-(5-amino-2-{2-[4-(2-{2-[2-(diethoxyphosphoryl)ethoxy]ethoxy}ethoxy)-2-methylphenyl]ethyl}benzo[f]1,7-naphthyridin-8-yl)propanoate (15).

Step 13: 3-(5-amino-2-(2-methyl-4-(2-(2-(2-phosphonoethoxyl)ethoxy)ethoxy)phenethyl)benzo[f][1,7]naphthyridin-8-yl)propanoic acid (16)

To a solution of ethyl 3-(5-amino-2-{2-[4-(2-{2-[2-(diethoxyphosphoryl)ethoxy]ethoxy}ethoxy)-2-methylphenyl]ethyl}benzo[f]1,7-naphthyridin-8-yl)propanoate (15) (1.0 equiv.) in DCM (0.16M) at 0° C. was added slowly TMSBr (10 equiv.). The reaction was stirred at room temperature overnight. Additional TMSBr (5.0 equiv.) was added at 0° C., and the reaction was again stirred at room temperature overnight. The solvent was removed by evaporation and the crude orange solids dried on hi-vac briefly. The solids were suspended in EtOH (0.5M) and added 2.5N NaOH (10.0 equiv.). The reaction was stirred at 80° C. for 3 hours. After cooling to room temperature, the mixture was adjusted to pH 9 to 10 and directly purified on RP-HPLC using a C18 column, eluting with 10-40% 95:5 (MeCN/5 mM NH$_4$OAc) in 10 mM NH$_4$OAc (pH 9) gradient. The fractions containing the product were combined and concentrated in vacuo. The resulting white gel was dissolved in refluxing 1:1 EtOH/water (0.04M) with the addition of a few drops of ammonium hydroxide. While hot, the mixture was slowly poured into a stirring hot solution of acetone (0.009M) preheated at 50° C. The acetone suspension was slowly cooled to room temperature for 15 minutes with continued stirring, and then sat in an ice bath for 10 minutes. The solids were filtered and washed successively with acetone (2×) and ether (2×). The solids were dried on hi-vac overnight to give compound (16) as a solid. The $^1$H NMR (Dimethylsulfoxide-d6) obtained for 3-(5-amino-2-(2-methyl-4-(2-(2-(2-phosphonoethoxyl)ethoxy)ethoxy)phenethyl)benzo[f][1,7]naphthyridin-8-yl)propanoic acid was: δ 9.02 (s, 1H), 8.82 (s, 1H), 8.55 (d, 1H, J=8.0 Hz), 7.58 (s, 1H), 7.49 (d, 1H, J=8.4 Hz), 7.06 (d, 1H, J=8.0 Hz), 6.76 (s, 1H), 6.68 (d, 1H, J=8.0 Hz), 4.03-4.00 (m, 2H), 3.71-3.69 (m, 2H), 3.60-3.54 (m, 4H), 3.51-3.49 (m, 2H), 3.16-3.12 (m, 2H), 3.03-2.96 (m, 4H), 2.67-2.66 (m, 2H), 2.33-2.32 (m, 2H), 2.26 (s, 3H). LRMS [M+H]=598.2.

Arginine Salt Formation 98.025 mg of 3-(5-amino-2-(2-methyl-4-(2-(2-(2-phosphonoethoxyl)ethoxy)ethoxy)phenethyl)benzo[f][1,7]naphthyridin-8-yl)propanoic acid were weighed into a glass vial and 1.7 ml of 0.1M arginine in 80/20 methanol/water was added to give a 57 mg/mL solution. The solution was slurried for 60 minutes at 50° C. 7 mL of ethanol was then added which resulted in a white fluffy precipitate following stirring for several hours. The solids were filtered and dried in a vacuum oven for 3 days at 40° C. to yield 110 mg of arginine salt of 3-(5-amino-2-(2-methyl-4-(2-(2-(2-phosphonoethoxyl)ethoxy)ethoxy)phenethyl)benzo[f][1,7]naphthyridin-8-yl)propanoic acid.

NMR Data

Figure 1A:
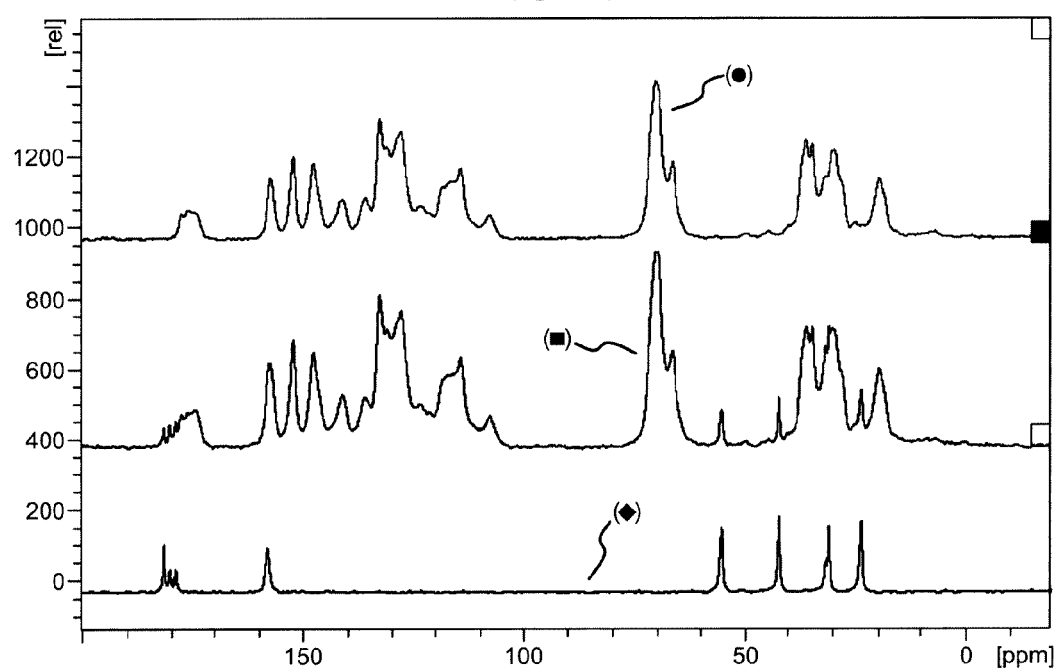
FIG. 1a shows the $^{13}$C NMR spectrum for a L-arginine salt of the compound of formula (I).
Figure 1B:
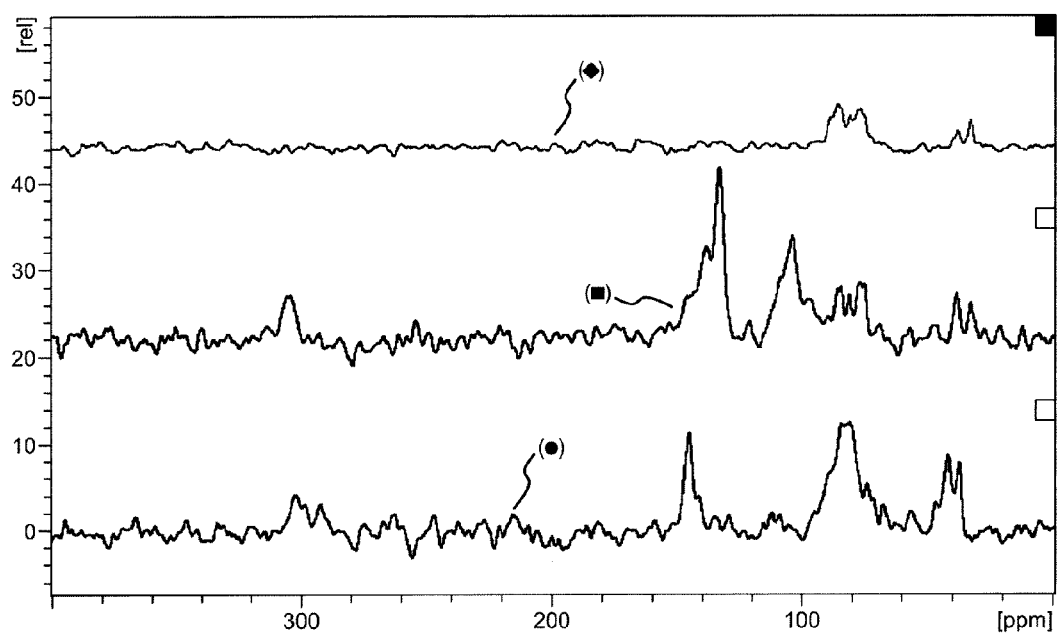
FIG. 1b shows the $^{15}$N NMR spectrum for a L-arginine salt of the compound of formula (I).

FIGS. 1a and 1b show NMR spectra for the L-arginine salt of the present invention compared to the free base. Arginine salt of the compound of formula (I) (■); free base (●); and free arginine (♦).

XRPD Data

Figure 2:
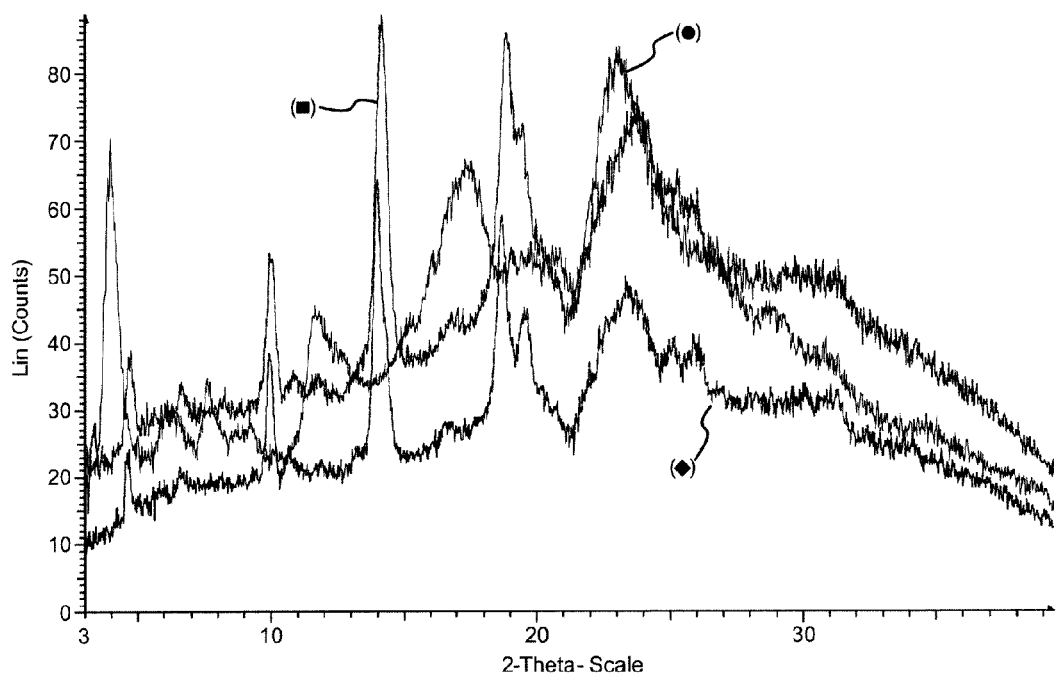
FIG. 2 shows XRPD patterns for a L-arginine salt and the free base.

FIG. 2 shows the XRPD data for the above obtained L-arginine salt compared to the free base. Arginine salt (100 mg (♦) and 1000 mg (■)) of the compound of formula (I); free base (●).

Stability Studies

The L-arginine salt formed via the above method was tested for thermal- and photo-stability. For comparative purposes, the free base and the ammonium salt were also tested.

The bulk ammonium and arginine salts and the bulk free base of the compound of formula (I) were tested for photo-stability by being irradiated (1.2 million lux-hours), at 40° C. for a period of 36 hours. The free base showed 12.36% degradation, the arginine salt showed 9.7% degradation and the ammonium salt showed 4.6% degradation.

The arginine salt and the bulk free base of the compound of formula (I) were also tested for photo-stability in a solution of 50 mM phosphate buffer (pH 6.8) by being irradiated (1.2 million lux-hours), at 40° C. for a period of 36 hours. The free base showed 23.1% degradation, the arginine salt showed 9.8% degradation. The ammonium salt was not tested.

The bulk ammonium and arginine salts and the bulk free base of the compound of formula (I) were also tested for thermal-stability at physiological pH (7.4) by heating at 80° C. for 7 days. After heating the free base showed 18.1% degradation compared to 0.1% degradation of the arginine salt.

Thus, the arginine salt showed improved thermal-stability at physiological pH and photo-stability compared to the free base. While the ammonium salt showed slightly better photo-stability than the arginine salt, the ammonium salt presents other drawbacks, in particular that the degradation products are toxic ammonia gas. This renders the ammonium salt unsuitable for use in pharmaceutical formulation and long term storage. Furthermore, at high temperatures (80° C.), such as those used during the sterilisation procedures encompassed by the invention (e.g. autoclaving) the arginine salt is more stable than the ammonium salt. The arginine salt is also more stable than the free base at the high temperatures (80° C.) used in autoclaving.

Stoichiometric Confirmation

Elemental analysis was conducted on the arginine salt produced above. The analysis is shown in the table below.

| % C | Target | % Diff | % H | Target | % Diff | % N | Target | % Diff | % P | Target | % Diff | % H$_2$O |
|---|---|---|---|---|---|---|---|---|---|---|---|---|
| 53.93 | 53.52 | −0.77 | 6.74 | 6.74 | 0.00 | 12.14 | 12.70 | 4.41 | 3.59 | 3.83 | 6.27 | 3.81 |

This analysis confirms a 1:1 stoichiometry between the compound of formula (I) and L-arginine. The target is the theoretical monohydrate salt of the compound of formula (I) as described herein.

Thermal Analysis

The L-arginine salt produced above was analysed via thermogravimetric analysis (TGA) and differential scanning calorimetry (DSC). The results are shown in FIG. 1.

Water Sorption

Figure 3:
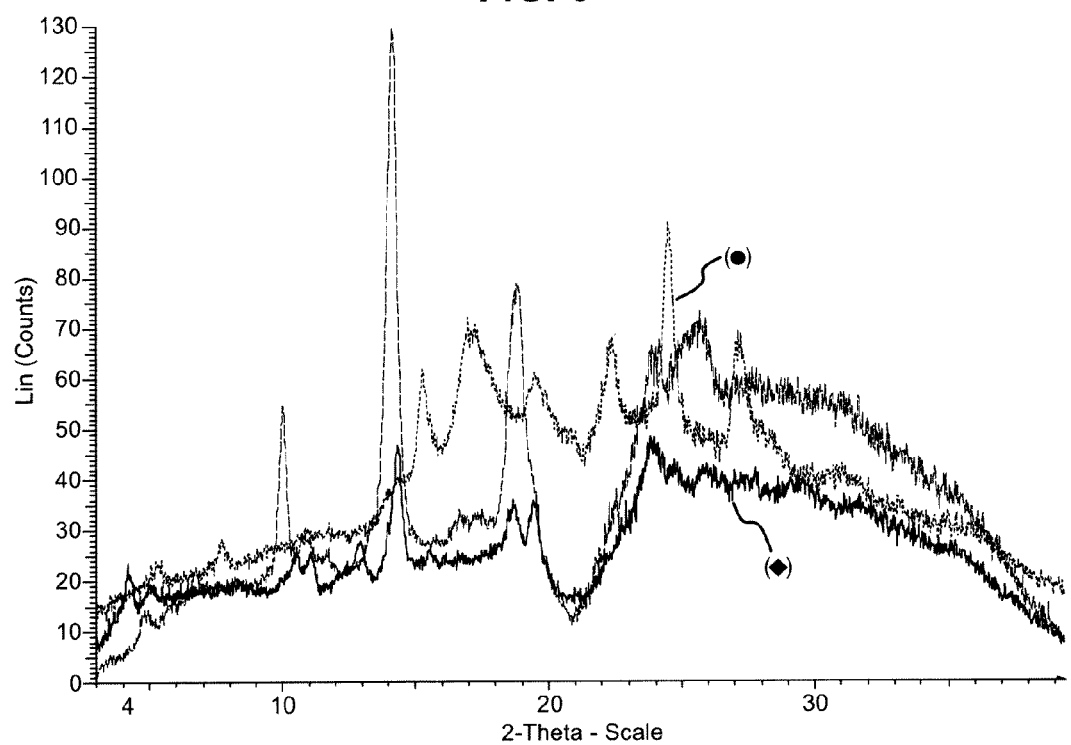
FIG. 3 shows XRPD patterns for a L-arginine salt of the compound of formula (I) before and after DVS treatment.
Figure 4:
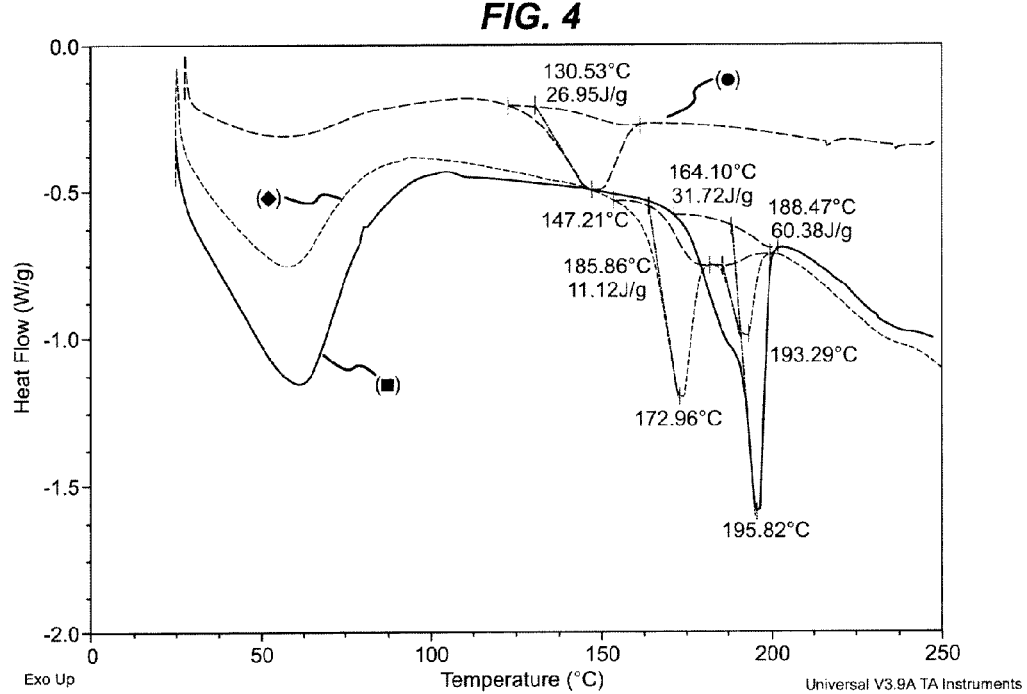
FIG. 4 shows DSC analysis for a L-arginine salt of the compound of formula (I) before and after DVS analysis.

Dynamic vapour sorption (DVS) experiments were conducted on the L-arginine salt obtained via the above method. The DVS analysis again shows that the arginine salt is hygroscopic, taking on approximately 18% water at 90% relative humidity. XRPD for the salt pre- (♦) and post-DVS (■) are shown in FIG. 3. The free base is also shown for comparison (●). DSC analysis of the arginine salt following DVS treatment was also conducted and the results pre- (♦) and post-DVS (■) treatment are shown in FIG. 4. The free base is also shown for comparison (●).

Figure 3A:
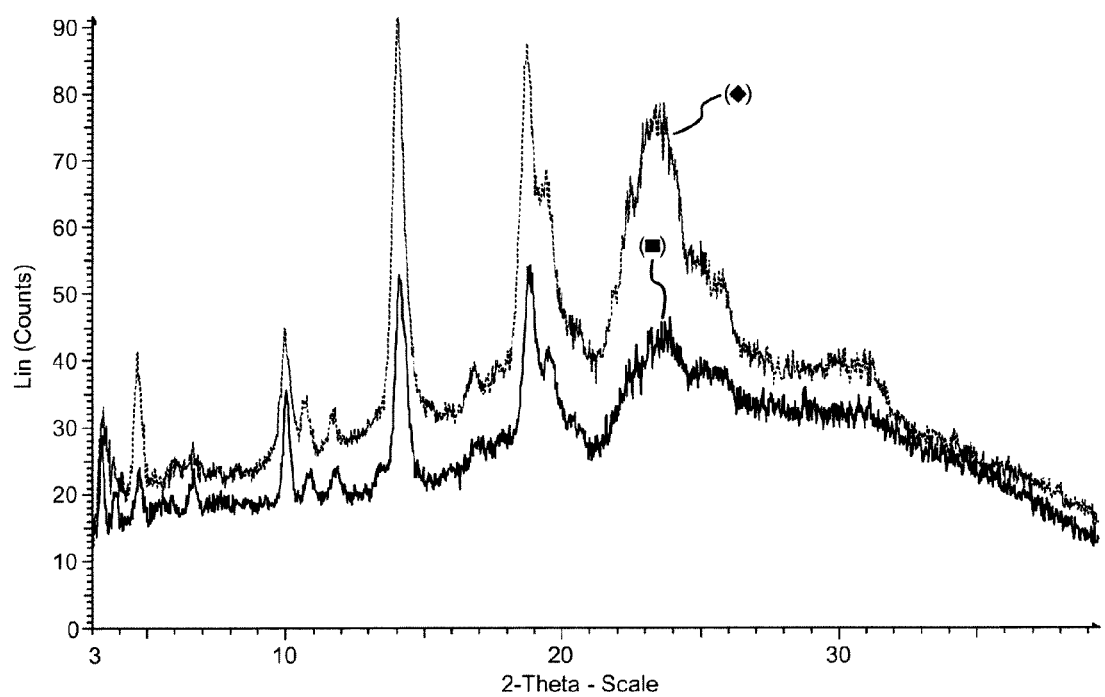
FIG. 3a shows XRPD patterns for a 4 g sample of a L-arginine salt of the compound of formula (I) before and after DVS treatment.

DVS was also performed on a 4 g sample of the L-arginine salt of the compound of formula (I) described herein. The DVS analysis again shows that the arginine salt is hygroscopic, taking on approximately 13.71% water at 90% relative humidity. After two cycles, the same amount of water is shown to be adsorbed and desorbed, which indicates that no further hydrates were formed (which would have a negative impact on solubility). No form change is noted by the XRPD. XRPD for the salt pre- (♦) and post-DVS (■) are shown in FIG. 3a.

Adsorption Studies—Aluminium Phosphate

Adsorption of a L-arginine salt of the compound of formula (I) to a commercially-available aluminium phosphate adjuvant yielded an adsorption efficiency of 97% (as found by recovering the compound of formula (I) on desorption). Pretreatment of the aluminium phosphate adjuvant with inorganic phosphate (potassium phosphate) had an impact on the adsorption capacity, and adsorption was inhibited in a concentration dependent manner. However, the adsorption remained >90% when the aluminium phosphate adjuvant was treated with 10 mM potassium phosphate.

One formulation was prepared with 0.4 mg/ml of the compound of formula (I) of the L-arginine salt and 3 mg/ml of aluminium phosphate (expressed as $Al^{3+}$ concentration), 10 mM of histidine buffer (pH 6.5). Aluminium phosphate was treated overnight with various concentrations of potassium phosphate (10 mM, 50 mM, 100 mM, 250 mM and 500 mM) before the compound of formula (I) of the arginine salt was incubated with the aluminium phosphate.

| | Pre-treatment with potassium phosphate (mM) | | | | |
|---|---|---|---|---|---|
| 0 | 10 | 50 | 100 | 250 | 500 |
| % Adsorption | | | | | |
| 97 ± 1 | 93 ± 1 | 81.6 ± 0.1 | 60 ± 2 | 52 ± 0.1 | 65 ± 4 |

Adsorption Studies—Aluminium Hydroxide

The L-arginine salt of the compound of formula (I) was tested for adsorption at 1 mg/ml concentration on 3 mg/ml aluminium hydroxide ("Al—H"). The adsorption efficiency of the compound was determined by RP-HPLC as being 99%.

Adsorption Studies—Calcium Phosphate

Adsorption of a L-arginine salt of the compound of formula (I) to a commercially-available calcium phosphate adjuvant was studied at pH 6.4, without histidine buffer. Two formulations are prepared, both with 1.12 mg/ml $Ca^{2+}$ but with either 0.25 mg/ml or 0.125 mg/ml of the arginine salt. Adsorption was around 90% for both formulations.

Systemic Exposure after In Vivo Delivery

Adsorption of the compound of formula (I) on Al—H reduced its peak serum concentrations and increased residence times at sites of intramuscular injection, as found for mice and rats preclinical species. This contributes greatly on modifying and controlling the level of systemic exposure avoiding the potential problem of proinflammatory cytokines in the blood, improving safety and/or tolerability of the compounds of formula (I).

A single dose of two different formulations (one containing the free base and the other the L-arginine salt of the compound of formula (I)) adsorbed to Al—H in 10 mM histidine buffer and in the presence of 3 MenB antigens were administered intramuscularly to mice at a dose of 4 mg/kg. The free base formulation had a $T_{1/2}$ of 9.5 hours, $T_{max}$ of 0.83 hours, $C_{max}$ of 465 nM and $AUC_{0-24}$ of 4552 h*nM. The compound of formula (I) had a $T_{1/2}$ of 8.48 hours, $T_{max}$ of 0.67 hours, $C_{max}$ of 453 nM and $AUC_{0-24}$ of 4538 h*nM.

Meningococcus B

Reference 12 discloses a vaccine for serogroup B meningococcus ("MenB") made from three separate polypeptides (see also reference 46). These three polypeptides can adsorb to aluminium hydroxide ("Al—H"), and this adsorption still occurs after the arginine salt of compound (I) is pre-adsorbed to the Al—H.

A modified version of this 3-valent MenB vaccine was tested in which the GNA2091-1870 fusion protein was replaced by "936-10A-10A" as disclosed in reference 43. This mixture of proteins was tested with the compound of formula (I) as free base or as the arginine salt, at two different strengths. Sera from immunised mice with the vaccine intraperitoneally (IP) or intramuscularly (IM), and then sera were tested in a bactericidal assay (SBA) against 5 different strains. Bactericidal titers were as follows:

| | | MC58 | NZ | 961-5945 | UK355 | 5-99 |
|---|---|---|---|---|---|---|
| Al—H | IP | 4096 | 2048 | ≥8192 | 512 | ≥8192 |
| Al—H/50 µg free base | IP | ≥8192 | ≥8192 | ≥8192 | ≥8192 | ≥8192 |
| Al—H/50 µg Arg salt | IP | ≥8192 | ≥8192 | ≥8192 | ≥8192 | ≥8192 |
| Al—H/25 µg free base | IP | ≥8192 | ≥8192 | ≥8192 | ≥8192 | ≥8192 |
| Al—H/25 µg Arg salt | IP | ≥8192 | ≥8192 | ≥8192 | ≥8192 | ≥8192 |
| Al—H | IM | 4096 | 1024 | ≥8192 | 256 | ≥8192 |
| Al—H/50 µg free base | IM | ≥8192 | ≥8192 | ≥8192 | 4096 | ≥8192 |
| Al—H/50 µg Arg salt | IM | ≥8192 | ≥8192 | ≥8192 | 2048 | ≥8192 |

Thus the free base and the Arg salt both improved responses relative to Al—H alone, and could provide high titers against all strains in the panel, achieving a titer of ≥8192 against all strains when administered by the IP route, thereby improving the strain coverage of the vaccine.

Moreover, the results indicate that adsorption of the compound as a free base or as the L-arginine salt does not change bioequivalence by the SBA test.

RSV

Figure 5:
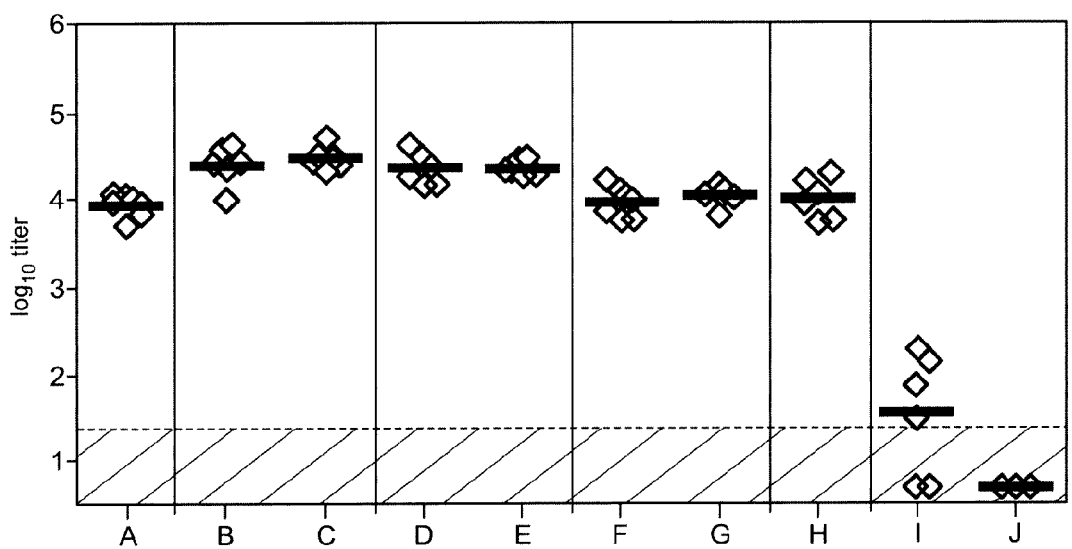
FIG. 5 shows $\log_{10}$ anti-RSV titers for 10 groups: (A) Al—H alone; (B) 50 µg SMIP, free base; (C) 50 µg SMIP, arginine salt; (D) 5 µg SMIP, free base; (E) 5 µg SMIP, arginine salt; (F) 1 µg SMIP, free base; (G) 1 µg SMIP, arginine salt; (H) IC31; (I) unadjuvanted; (J) buffer alone.

Trimeric F glycoprotein (3 µg) of respiratory syncytial virus (RSV) is formulated with the compound of formula (I) as a free base or as the arginine salt (1 µg, 5 µg, 50 µg) adsorbed to Al—H. For comparison the IC31™ adjuvant is also tested. Balb/C mice (6 per group) are immunized at days 0 and 21 and immune responses are assessed. Titers 3 weeks after the first dose are shown in FIG. 5. At all 3 doses of SMIP the arginine salt (FIG. 5, groups C, E, G) gives slightly higher titers than the free base (groups B, D, F), and titers are increased compared to Al—H alone (group A).

It will be understood that the invention has been described by way of example only and modifications may be made while remaining within the scope and spirit of the invention.

REFERENCES

[1] WO2011/027222
[2] PCT/US2011/050231
[3] Burrell et al. (1999) Vaccine 17:2599-603.
[4] *Vaccine Design* . . . (1995) eds. Powell & Newman. ISBN: 030644867X. Plenum.
[5] Clausi et al. (2008) J Pharm Sci DOI 10.1002/jps.21390.
[6] Treanor et al. (1996) J Infect Dis 173:1467-70.
[7] Keitel et al. (1996) Clin Diagn Lab Immunol 3:507-10.
[8] WO03/097091.
[9] Cassone & Torosantucci (2006) Expert Rev Vaccines 5:859-67.
[10] WO2010/140119.
[11] WO2010/119343.
[12] Giuliani et al. (2006) Proc Natl Acad Sci USA. 103: 10834-9.
[13] WO95/27787.
[14] WO03/010317.
[15] WO2007/110700.
[16] WO2006/138004.
[17] WO2005/084306.
[18] WO2005/002619.
[19] WO03/049762.
[20] WO02/02606.
[21] WO00/37494.
[22] WO2008/020330.
[23] WO2006/091517.
[24] WO2006/089264.
[25] Covacci & Rappuoli (2000) J. Exp. Med. 19:587-592.
[26] WO 93/18150.
[27] Covacci et al. (1993) Proc. Natl. Acad. Sci. USA 90:5791-5795.
[28] Tummuru et al. (1994) Infect. Immun. 61:1799-1809.
[29] Marchetti et al. (1998) Vaccine 16:33-37.
[30] Telford et al. (1994) J. Exp. Med. 179:1653-1658.
[31] Evans et al. (1995) Gene 153:123-127.
[32] WO 96/01272 & WO96/01273, especially SEQ ID NO:6.
[33] WO 97/25429.
[34] Rappuoli et al. (1991) TIBTECH 9:232-238.
[35] Nencioni et al. (1991) Infect Immun. 59(2): 625-30.
[36] Dasarai et al. (2011) J Gen Virol PMID: 21307228.
[37] Zhang et al. (2001) J. Biol. Chem. 276:39577-85.
[38] Earl et al. (2001) J Virol 75:645-53.
[39] Barnett et al. (2001) J Virol 75:5526-40.
[40] MMWR Morb Mortal Wkly Rep 1998 Jan. 16; 47(1):12, 19.
[41] Harper et al. (2004) Lancet 364(9447):1757-65.
[42] U.S. Pat. No. 6,699,474.
[43] WO2011/024072.
[44] WO2007/060548.
[45] WO2009050586.
[46] WO2004/032958.
[47] Remington: The Science and Practice of Pharmacy (Gennaro, 2000; 20th edition, ISBN: 0683306472).

SEQUENCE LISTING

SEQ ID NO: 1
ATNDDDVKKAATVAIAAAYNNGQEINGFKAGETIYDIDEDGTITKKDATA
ADVEADDFKGLGLKKVVTNLTKTVNENKQNVDAKVKAAESEIEKLTTKLA
DTDAALADTDAALDATTNALNKLGENITTFAEETKTNIVKIDEKLEAVAD
TVDKHAEAFNDIADSLDETNTKADEAVKTANEAKQTAEETKQNVDAKVKA
AETAAGKAEAAAGTANTAADKAEAVAAKVTDIKADIATNKDNIAKKANSA
DVYTREESDSKFVRIDGLNATTEKLDTRLASAEKSIADHDTRLNGLDKTV
SDLRKETRQGLAEQAALSGLFQPYNVG

SEQ ID NO: 2
MASPDVKSADTLSKPAAPVVSEKETEAKEDAPQAGSQGQGAPSAQGGQDM
AAVSEENTGNGGAAATDKPKNEDEGAQNDMPQNAADTDSLTPNHTPASNM
PAGNMENQAPDAGESEQPANQPDMANTADGMQGDDPSAGGENAGNTAAQG
TNQAENNQTAGSQNPASSTNPSATNSGGDFGRTNVGNSVVIDGPSQNITL
THCKGDSCSGNNFLDEEVQLKSEFEKLSDADKISNYKKDGKNDGKNDKFV
GLVADSVQMKGINQYIIFYKPKPTSFARFRRSARSRRSLPAEMPLIPVNQ
ADTLIVDGEAVSLTGHSGNIFAPEGNYRYLTYGAEKLPGGSYALRVQGEP
SKGEMLAGTAVYNGEVLHFHTENGRPSPSRGRFAAKVDFGSKSVDGIIDS
GDGLHMGTQKFKAAIDGNGFKGTWTENGGGDVSGKFYGPAGEEVAGKYSY
RPTDAEKGGFGVFAGKKEQDGSGGGGATYKVDEYHANARFAIDHFNTSTN
VGGFYGLTGSVEFDQAKRDGKIDITIPVANLQSGSQHFTDHLKSADIFDA
AQYPDIRFVSTKFNFNGKKLVSVDGNLTMHGKTAPVKLKAEKFNCYQSPM
AKTEVCGGDFSTTIDRTKWGVDYLVNVGMTKSVRIDIQIEAAKQ

SEQ ID NO: 3
MVSAVIGSAAVGAKSAVDRRTTGAQTDDNVMALRIETTARSYLRQNNQTK
GYTPQISVVGYDRHLLLLGQVATEGEKQFVGQIARSEQAAEGVYNYITVA
SLPRTAGDIAGDTWNTSKVRATLLGISPATRARVKIVTYGNVTYVMGILT
PEEQAQITQKVSTTVGVQKVITLYQNYVQRGSGGGGVAADIGAGLADALT
APLDHKDKGLQSLTLDQSVRKNEKLKLAAQGAEKTYGNGDSLNTGKLKND
KVSRFDFIRQIEVDGQLITLESGEFQVYKQSHSALTAFQTEQIQDSEHSG
KMVAKRQFRIGDIAGEHTSFDKLPEGGRATYRGTAFGSDDAGGKLTYTID
FAAKQGNGKIEHLKSPELNVDLAAADIKPDGKRHAVISGSVLYNQAEKGS
YSLGIFGGKAQEVAGSAEVKTVNGIRHIGLAAKQ

SEQ ID NO: 4
MVSAVIGSAAVGAKSAVDRRTTGAQTDDNVMALRIETTARSYLRQNNQTK
GYTPQISVVGYDRHLLLLGQVATEGEKQFVGQIARSEQAAEGVYNYITVA
SLPRTAGDIAGDTWNTSKVRATLLGISPATRARVKIVTYGNVTYVMGILT
PEEQAQITQKVSTTVGVQKVITLYQNYVQRGSGGGGVAADIGAGLADALT
APLDHKDKGLQSLTLDQSVRKNEKLKLAAQGAEKTYGNGDSLNTGKLKND
KVSRFDFIRQIEVDGQLITLESGEFQVYKQSHSALTAFQTEQIQDSEHSG
KMVAKRQFRIGDLGGEHTAFNQLPDGKAEYRGTAFGSDDAGGKLTYTIDF
TKKQGNGKIEHLKSPELNVELASAEIKADGKSHAVILGDVRYGSEEKGSY
SLGIFGGRAQEVAGSAEVKTVNGIRHIGLAAKQGSGGGGVAADIGAGLAD
ALTAPLDHKDKGLQSLTLDQSVRKNEKLKLAAQGAEKTYGNGDSLNTGKL
KNDKVSRFDFIRQIEVDGQLITLESGEFQVYKQSHSALTAFQTEQIQDSE
HSGKMVAKRQFRIGDLGGEHTAFNQLPDGKAEYRGTAFGSDDAGGKLTYT
IDFTKKQGNGKIEHLKSPELNVELASAEIKADGKSHAVILGDVRYGSEEK
GSYSLGIFGGRAQEVAGSAEVKTVNGIRHIGLAAKQ

SEQ ID NO: 5
MGPDSDRLQQRRVAADIGAGLADALTAPLDHKDKSLQSLTLDQSVRKNEK
LKLAAQGAEKTYGNGDSLNTGKLKNDKVSRFDFIRQIEVDGQLITLESGE
FQIYKQDHSAVVALQIEKINNPDKIDSLINQRSFLVSGLGGEHTAFNQLP
DGKAEYHGKAFSSDDAGGKLTYTIDFAAKQGHGKIEHLKTPEQNVELAAA
ELKADEKSHAVILGDTRYGSEEKGTYHLALFGDRAQEIAGSATVKIGEKV
HEIGIAGKQGSGGGGVAADIGAGLADALTAPLDHKDKGLQSLTLDQSVRK
NEKLKLAAQGAEKTYGNGDSLNTGKLKNDKVSRFDFIRQIEVDGQLITLE
SGEFQVYKQSHSALTAFQTEQIQDSEHSGKMVAKRQFRIGDIAGEHTSFD
KLPEGGRATYRGTAFGSDDAGGKLTYTIDFAAKQGNGKIEHLKSPELNVD
LAAADIKPDGKRHAVISGSVLYNQAEKGSYSLGIFGGKAQEVAGSAEVKT
VNGIRHIGLAAKQGSGPDSDRLQQRRVAADIGTGLADALTAPLDHKDKGL
KSLTLEDSIPQNGTLTLSAQGAEKTFKAGDKDNSLNTGKLKNDKISRFDE
VQKIEVDGQTITLASGEFQIYKQNHSAVVALQIEKINNPDKTDSLINQRS
FLVSGLGGEHTAFNQLPGGKAEYHGKAFSSDDPNGRLHYSIDFTKKQGYG
RIEHLKTLEQNVELAAAELKADEKSHAVILGDTRYGSEEKGTYHLALFGD
RAQEIAGSATVKIGEKVHEIGIAGKQ

The invention claimed is:

1. An arginine salt of 3-(5-amino-2-(2-methyl-4-(2-(2-(2-phosphonoethoxy)ethoxy)ethoxy)phenethyl)benzo[f][1,7]naphthyridin-8-yl)propanoic acid.

2. The salt of claim 1, wherein the salt has a 1:1 stoichiometry of arginine to 3-(5-amino-2-(2-methyl-4-(2-(2-(2-phosphonoethoxy)ethoxy)ethoxy)phenethyl)benzo[f][1,7]naphthyridin-8-yl)propanoic acid.

3. The salt of claim 1, wherein the arginine salt is an L-arginine salt.

4. The salt of claim 1, wherein the salt is hydrated.

5. The salt of claim 1, wherein the salt is a monohydrate.

6. The salt of claim 1, wherein the salt is a substantially amorphous solid.

7. A method of raising an immune response in a subject comprising administering to the subject a therapeutically effective amount of a salt of claim 1.

8. A process for the preparation of the arginine salt of claim 1, comprising the step of contacting 3-(5-amino-2-(2-methyl-4-(2-(2-(2-phosphonoethoxy)ethoxy)ethoxy)phenethyl)benzo[f][1,7]naphthyridin-8-yl)propanoic acid with arginine in an solvent.

9. A composition comprising an arginine salt of 3-(5-amino-2-(2-methyl-4-(2-(2-(2-phosphonoethoxy)ethoxy)ethoxy)phenethyl)benzo[f][1,7]naphthyridin-8-yl)propanoic acid and an insoluble metal salt.

10. The composition of claim 9, further comprising an immunogen.

11. A process for preparing an adjuvant complex, comprising a step of mixing an arginine salt of 3-(5-amino-2-(2-methyl-4-(2-(2-(2-phosphonoethoxy)ethoxy)ethoxy)phenethyl)benzo[f][1,7]naphthyridin-8-yl)propanoic acid with an insoluble metal salt such that the acid adsorbs to the insoluble metal salt to form the complex.

12. A compound of (Ia):

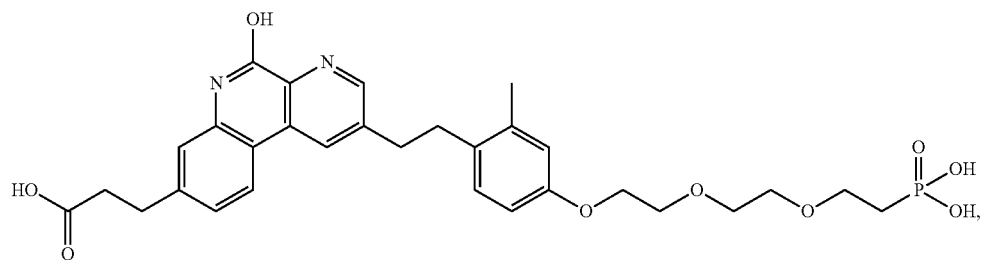

or an arginine salt or solvate thereof.

13. An L-arginine salt of 3-(5-amino-2-(2-methyl-4-(2-(2-(2-phosphonoethoxy)ethoxy)ethoxy)phenethyl)benzo[1,7]naphthyridin-8-yl)propanoic acid having a 1:1 stoichiometry of arginine to 3-(5-amino-2-(2-methyl-4-(2-(2-(2-phosphonoethoxy)ethoxy)ethoxy)phenethyl)benzo[f][1,7]naphthyridin-8-yl)propanoic acid.

14. The salt of claim 13, wherein the salt is hydrated.

15. The salt of claim 13, wherein the salt is a monohydrate.

16. The salt of claim 13, wherein the salt is a substantially amorphous solid.

17. A method of raising an immune response in a subject comprising administering to the subject a therapeutically effective amount of a salt of claim 2.

* * * * *